(12) United States Patent
Nichols

(10) Patent No.: US 7,956,065 B2
(45) Date of Patent: Jun. 7, 2011

(54) PHARMACEUTICAL COMPOUNDS

(75) Inventor: Philip Paul Nichols, Newcastle (GB)

(73) Assignee: Biovail Laboratories International (Barbados) S.R.L., Christ Church (BB)

(*) Notice: Subject to any disclaimer, the term of this patent is extended or adjusted under 35 U.S.C. 154(b) by 0 days.

(21) Appl. No.: 12/555,695

(22) Filed: Sep. 8, 2009

(65) Prior Publication Data

US 2010/0063086 A1   Mar. 11, 2010

(30) Foreign Application Priority Data

Sep. 8, 2008 (GB) .................................. 0816371.9

(51) Int. Cl.
*A61K 31/435* (2006.01)
(52) U.S. Cl. ....................................................... 514/294
(58) Field of Classification Search .................. 514/294
See application file for complete search history.

(56) References Cited

U.S. PATENT DOCUMENTS

| | | | |
|---|---|---|---|
| 2,830,993 A | 4/1958 | Brossi et al. |
| 2,843,591 A | 7/1958 | Brossi et al. |
| 2,954,382 A | 9/1960 | Osbond |
| 3,009,918 A | 11/1961 | Openshaw et al. |
| 3,045,021 A | 7/1962 | Brossi |
| 3,053,845 A | 9/1962 | Tretter |
| 3,079,395 A | 2/1963 | Brossi et al. |
| 3,095,419 A | 6/1963 | Tretter |
| 3,105,079 A | 9/1963 | Tretter |
| 3,123,609 A | 3/1964 | Openshaw et al. |
| 3,132,147 A | 5/1964 | Schopf et al. |
| 3,159,638 A | 12/1964 | Ritchie et al. |
| 3,209,005 A | 9/1965 | Brossi et al. |
| 3,314,966 A | 4/1967 | Brossi et al. |
| 3,342,825 A | 9/1967 | Openshaw et al. |
| 3,375,254 A | 3/1968 | Openshaw et al. |
| 3,390,152 A | 6/1968 | Harnden |
| 3,634,431 A | 1/1972 | Van Dyke |
| 3,635,986 A | 1/1972 | Van Dyke |
| 4,076,820 A | 2/1978 | Archibald et al. |
| 4,102,886 A | 7/1978 | Szantay et al. |
| 4,133,812 A | 1/1979 | Szaantay et al. |
| 4,304,913 A | 12/1981 | Havera et al. |
| 4,353,656 A | 10/1982 | Sohl et al. |
| 4,778,054 A | 10/1988 | Newell et al. |
| 4,811,731 A | 3/1989 | Newell et al. |
| 5,035,237 A | 7/1991 | Newell et al. |
| 5,590,645 A | 1/1997 | Davies et al. |
| 5,860,419 A | 1/1999 | Davies et al. |
| 5,873,360 A | 2/1999 | Davies et al. |
| 6,087,376 A | 7/2000 | Crooks et al. |

(Continued)

FOREIGN PATENT DOCUMENTS

EP      0069715 A1    1/1983

(Continued)

OTHER PUBLICATIONS

"U.S. Appl. No. 10/597,803, Final Office Action mailed Oct. 27, 2009", 22 Pgs.

(Continued)

*Primary Examiner* — Jennifer M Kim
(74) *Attorney, Agent, or Firm* — Schwegman, Lundberg & Woessner, P.A.

(57) ABSTRACT

This application describes method of treating dementia and cognitive deficits associated with dementia that involve administration of dihydrotetrabenazine, and isomers and/or pharmaceutically acceptable salts thereof.

10 Claims, 2 Drawing Sheets

U.S. PATENT DOCUMENTS

| | | | |
|---|---|---|---|
| 6,462,069 B2 | 10/2002 | Reich et al. |
| 6,482,986 B1 | 11/2002 | Boigegrain et al. |
| 6,632,666 B2 | 10/2003 | Baust et al. |
| 2005/0064034 A1 | 3/2005 | Li et al. |
| 2006/0173011 A1 | 8/2006 | Shin et al. |
| 2008/0108645 A1 | 5/2008 | Tridgett et al. |
| 2008/0319000 A1 | 12/2008 | Tridgett |
| 2009/0275605 A1 | 11/2009 | Duffield et al. |
| 2010/0055133 A1 | 3/2010 | Duffield et al. |
| 2010/0063086 A1 | 3/2010 | Nichols |
| 2010/0087475 A1 | 4/2010 | Duffield et al. |
| 2010/0087476 A1 | 4/2010 | Duffield et al. |
| 2011/0053866 A1 | 3/2011 | Duffield et al. |

FOREIGN PATENT DOCUMENTS

| | | | |
|---|---|---|---|
| EP | 0839805 A1 | 6/1998 |
| GB | 2064336 A | 6/1981 |
| GB | 2129691 A | 5/1984 |
| GB | 2169265 A | 7/1986 |
| GB | 2178965 A | 2/1987 |
| GB | 2242134 A | 9/1991 |
| GB | 2410947 A | 8/2005 |
| GB | 2463452 A | 3/2010 |
| WO | WO-2005077946 A1 | 8/2005 |
| WO | WO-2006069030 A1 | 6/2006 |
| WO | WO-2007007105 A1 | 1/2007 |
| WO | WO-2007017643 A1 | 2/2007 |
| WO | WO-2007017654 A1 | 2/2007 |
| WO | WO-2008079404 A2 | 7/2008 |
| WO | WO2009150474 A1 | 12/2009 |
| WO | WO2011019956 A2 | 2/2011 |

OTHER PUBLICATIONS

"U.S. Appl. No. 10/597,803, Response filed Jul. 29, 2009 to Non Final Office Action mailed Jan. 29, 2009", 26 pgs.

"European Application Serial No. 05708289.3, Response filed Sep. 17, 2007", 8 pgs.

"International Application Serial No. PCT/GB2005/000464, International Search Report mailed Jun. 10, 2005", 4 pgs.

"International Application Serial No. PCT/GB2005/000464, Preliminary Report on Patentability mailed Aug. 14, 2006", 9 pgs.

"International Application Serial No. PCT/GB2005/000464, Written Opinion mailed Jun. 10, 2005", 8 pgs.

"SYNKEM European DMF for Tetrabenazine", (Sep. 2005), 145 pgs.

Albin, R. L, et al., "Increased ventral striatal monoaminergic innervation in Tourette syndrome", Neurology, 61(3), (Aug. 12, 2003), 310-5.

Aranda, G., et al., "Synthesis and biological activity of iodinated and photosensitive derivatives of tetrabenazine", European Journal of Medicinal Chemistry, 25(4), (May 1990), 369-374.

Balkissoon, Ronald, "Asthma Overview", Primary Care: Clinics in Office Practice, vol. 35, Iss 1, (Mar. 2008), 41-60.

Berge, Stephen M, et al., "Pharmaceutical Salts", J. Pharm Sci., 66(1), (1977), 1-19.

Bohnen, N. I, et al., "Decreased striatal monoaminergic terminals in Huntington disease", Neurology, 54(9), (May 9, 2000), 1753-9.

Brossi, et al., "Syntheseversuche in der Emetin-Reihe 3. Mitteilung: 2-Hydroxy-hydrobenzo[a]chinolizine", Helvetica Chimica Acta vol. XLI, No. 193, (1958), 1793-1806.

Brossi, et al., "Syntheseversuche in der Emetin-Reihe 4. Mitteilung: Racemisches 2-Dehydro-emetin", Helvetica Chimica Acta vol. 42, (1959), 772-788.

Brossi, et al., "Syntheseversuche in der Emetin-Reihe 7. Mitteilung: Abbau und Synthese substituierter 2-Oxo-hydrobenzo[a]chinolizine", Helvetica Chimica Acta, vol. XLIII, No. 77, (1960), 583-593.

Brossi, et al., "Syntheseversuche in der Emetinreihe 9. Mitteilung: Die Absolute Konfiguration von (-)-2-Dehydro-emetin", Helvetica Chimica Acta, vol. XLV No. 257, (1962), 2219-2226.

Brossi, et al., "Synthetic Experiments in the Emetine Series", Helv. Chim. Acta. vol. XLI, No. 193, (1958), 119-139.

Brossi, A., et al., "Synthese und absolute Konfiguration von (-)-2-Dehydroemetin", Experentia, (1962), 211-212.

Brossi, A., et al., "Syntheseversuche in der Emetin-Reihe 2. Mitteilung: Neue Reaktionen mit 3,4-dihydro-isochinolinen", Chimia, 12, (1958), 114-115.

Brossi, A., et al., "Syntheseversuche in der Emetinreihe 8. Mitteilung Rac. Emetin-Isomere der 2,3-cis-Reihe", Helvetica Chimica Acta, 45(6), (1962), 1899-1907.

Brossi, V. A, et al., "Synthesen in der Emetin-Reihe", Arzneimittel Forschung, 15, (1965), 670-674.

Bruderer, et al., "Synthesen in der Emetin-Reihe 11. Mitteliung: 2-Aryisubstituierte Hydrobenzo[a]chinolizine", Helvetica Chimica Acta, 47(203), (1964), 1852-1860.

Canney, et al., "Amino- and Amido-Tetrabenazine Derivatives: Synthesis and Evaluation as Potential Ligands for the Vesicular Monoamine Transporter", Nucl. Med. Biol. 22, (1995), 527-535.

Dasilva, et al., "Characterization of [11C]Tetrabenazine as an in Vivo Radioligand for the Vesicular Monoamine Transporter", Nucl. Med. Biol vol. 21, No. 2, (1994), 151-156.

Dasilva, et al., "In Vivo Binding of [11C]Tetrabenazine to Vesicular Monoamine Transporters in Mouse Brain", Life Sciences vol. 51, (1992), 593-600.

Dasilva, et al., "In Vivo Imagine of Monoaminergic Nerve Terminals in Mormal and MPTP-Lesioned Primate Brain Using Positron Emission Tomography (PET) and [11C]Tetrabenazine", Synapse 14, (1993), 128-131.

Dasilva, J. N, et al., "Synthesis of a [11C]methoxy derivative of alpha-dihydrotetrabenazine: a radioligand for studying the vesicular monoamine transporter.", Appl Radiat Isot., 44(12), (Dec. 1993), 1487-9.

De Silva, Jean, et al., "Synthesis of [11C]Tetrabenazine, a Vesicular Monoamine Uptake Inhibitor, for PET Imaging Studies", Appl. Radiat. Isot. vol. 44: No. 4, (1993), 673-676.

Flack, et al., "Reporting and evaluating absolute-structure and absolute-configuration determinations", Journal of Applied Crystallography 33, (2000), 1143-1148.

Frey, et al., "Imagine of Monoaminergic and Cholinergic Vesicular Transporters in the Brain", Advances in Pharmacology vol. 42, (1998), 269-272.

Frey, et al., "Presynaptic Monoaminergic Vesicles in Parkinsons Disease and Normal Aging", Ann. Neurol. 40, (1996), 873-884.

Gerecke, M, et al., "Syntheseversuche in der Emetin-Reihe 10. Mitteilung: Zur Oxydation von 2-Dehydro-emetin-Verbindungen mit Quecksilber(II)-acetat", Helvetica Chimica Acta, vol. 47 No. 121, (1964), 1117-1123.

Gilman, et al., "Decreased Striatal Monoaminergic Terminals in Olivopontocerebellar Atrophy and Multiple System Atrophy Demonstrated with Positron Emission Tomography", Ann. Neurol 40, (1996), 885-892.

Jankovic, J., et al., "Long-term effects of tetrabenazine in hyperkinetic movement disorders.", Neurology, 48(2), (Feb. 1997), 358-62.

Jewett, et al., "A Simple Synthesis of [11C]Dihydrotetrabenazine (DTBZ)", Nuclear Medicine and Biology, vol. 24, (1997), 197-199.

Kilbourn, et al., "Absolute Configuration of (+)-alpha-Dihydrotetrabenazine, an Active Metabolite of Tetrabenazine", Chirality vol. 9, No. 1, (1997), 59-62.

Kilbourn, et al., "Binding of alpha-dihydrotetrabenazine to the vesicular monoamine transporter in stereospecific", Eur J Pharmacol, 278, (1995), 249-252.

Kilbourn, et al., "Differential Effects of Scopolamine on in Vivo Binding of Dopamine Transporter and Vesicular Monoamine Transporter Radioligands in Rat Brain", Experimental Nuerology 188, (2004), 387-390.

Kilbourn, et al., "Effects of Dopaminergic Drug Treatments on In Vivo Radioligand Binding to Brain Vesicular Monoamine Transporters", Nuclear Medicine and Biology vol. 23, (1996), 467-471.

Kilbourn, et al., "In Vitro and In Vivo Studies of Benzisoquinoline Ligands for the Brain Synaptic Vesicle Monoamine Transporter", J. Med. Chem. 39, (1996), 191-196.

Kilbourn, et al., "In Vivo Imagine of Vesicular Monoamine Transporters in Human Brain Using [11C]Tetrabenazine and Positron Emission Tomography", Journal of Neurochemistry, vol. 60, No. 6, (1993), 2315-2318.

Kilbourn, et al., "In Vivo Measures of Dopaminergic Radioligands in the Rat Brain: Rquilibrium Infusion Studies", Synapse 43, (2002), 188-194.

Kilbourn, "Long-term reproducibility of in vivo measures of specific binding of radioligands in rat brain", Nuclear Medicine and Biology 31, (2004), 591-595.

Kilbourn, et al., "Mutant Mouse Strains as Models for In Vivo Radiotracer Evaluations: [11C]Methoxytetrabenazine ([11C]MTBZ) in Tottering Mice", Nucl. Med. Biol. vol. 22, No. 5, (1995), 565-567.

Kilbourn, et al., "Pet Radioligands for Vesicular Neurotransmitter Transporters", Med. Chem. Res. 5, (1994), 113-126.

Kilbourn, et al., "Rapid and Differential Losses of In Vivo Dopamine Transporter (DAT) and Vesicular Monoamine Transporter (VMAT2) Radioligand Binding in MPTP-Treated Mice", Synapse 35, (2000), 250-255.

Kilbourn, et al., "The vesicular monoamine transporter is not regulated by dopaminergic drug treatments", Eur. J. Pharmacol., (1995), 577-583.

Kilbourn, "Time-Dependent Recovery of In Vivo Binding Sites after Drug Dosing: A Method of Radiotracer Evaluation", Nuclear Medicine and Biology vol. 24, (1997), 115-118.

Koeppe, et al., "Assessment of Extrastriatal Vesicular Monoamine Transporter Binding Site Density Using Stereoisomers of [11C]Dihydrotetrabenazine", Journal of Cerebral Blood Flow and Metabolism 19, (1999), 1376-1384.

Koeppe, et al., "Dual-[11C]Tracer Single-Acquisition Positron Emission Tomography Studies", Journal of Cerebral Blood Flow and Metabolism 21, (2001), 1480-1492.

Koeppe, et al., "Equilibrium Versus Compartmental Analysis for Assessment of the Vesicular Monoamine Transporter Using (+)-a_ [11C]Dihydrotetrabenazine (DTBZ) and Positron Emission Tomography", Journal of Cerebral Blood Flow and Metabolism 17, (1997), 919-931.

Koeppe, et al., "Kinetic Evaluation of [11C]Dihydrotetrabenazine by Dynamic PET: Measurement of Vesicular Monoamine Transporter", Journal of Cerebral Blood Flow and Metabolism 16, (1995), 1288-1299.

Mehvar, et al., "Concentration-Effect Relationships of Tetrabenazine and Dihydrotetrabenazine in the Rat", J. Pharm. Sci. 76 No. 6, (1987), 461-465.

Mehvar, et al., "Pharmacokinetics of Tetrabenazine and its Major Metabolite in Man and Rat", Drug Metab. Disp 15, (1987), 250-255.

Ondo, William G, et al., "Tetrabenazine treatment for tardive dyskinesia: assessment by randomized videotape protocol", Am J Psychiatry, 156(8), (Aug. 1999), 1279-81.

Osbond, J M, "Chemical Constitution and Amoebicidal Activity. Part VI. a New Systhesis of 2-Keytones and 2-Alcohols derived from 3-Alkyl-1,3,4,6,7,11b-hexahydro-9,10-dimethoxy-2H-benzo[a]quinolizines", J. Chem. Soc., (1961), 4711-4718.

Pletscher, A., et al., "Benzoquinolizine Derivatives: a New Class of Monamine Decreasing Drugs With Psychotropic Action", Int. Rev. Neurobiol., 4, (1962), 275-306.

Roberts, et al., "The Pharmacokinetics of Tetrabenazine and its Hydroxy Metabolite in Patients Treated for Involuntary Movement Disorders", European J. Clinical Pharmacology 29, (1986), 703-708.

Rubiralta, et al., "NMR Spectroscopy and X-Ray Crystallography of Benzo [a] Quinolizidines", Heterocycles 27, (1988), 1653-1664.

Scherman, et al., "Hydrophobicity of the Tetrabenazine-Binding Site of the Chromaffin Granule Monoamine Transporter", Molecular Pharmacology 33, (1988), 72-77.

Schwartz, et al., "Metabolic Studies of Tetrabenazine a Physotropic Drug in Animals and Man", Biochemical Pharmacology vol. 15, (1956), 645-655.

Uskokovic, et al., "The Nuclear Magnetic Resonance Spectra of the Angular Proton in Benzo [a]-and Indolo[a]quinolizidines", Journal of the American Chemical Society 86 (16), (1964), 3364-67.

Vander Borght, T. M, et al., "[3H]methoxytetrabenazine: a high specific activity ligand for estimating monoaminergic neuronal integrity", Neuroscience, 68(3), (Oct. 1995), 955-62.

Vander Borght, T. M, et al., "In vivo imaging of the brain vesicular monoamine transporter", J Nucl Med., 36(12), (Dec. 1995), 2252-60.

Williams, et al., "", Foye's Principles of Medicinal Chemistry, (2002), p. 50.

Zubieta, et al., "High Vesicular Monoamine Transporter Binding in Asymptomatic Bipolar I Disorder: Sex Differences and Cognitive Correlates", Am. J. Psychiatry 157:10, (2000), 1619-1628.

Boeve, Bradley F., "A Review of the Non-Alzheimer's Dementias", J. Clin. Psychiatry 67, (2006), 1985-2001.

Duisenberg, Albert J. M., "Indexing in Single-Crystal Diffractometry with an Obstinate List of Reflections", J. Appl. Cryst. 25, (1992), 92-96.

Ennaceur, A, et al., "A new one-trial test for neurobiological studies of memory in rats. 1: Behavioral data.", Behav. Brain Res., 31(1), (Nov. 1, 1988), 47-59.

Otwinowski, Zbyszek, et al., "Processing of X-Ray Diffraction Data Collected in Oscillation Mode", Methods in Enxymology, vol. 276 part A, (1997), 307-326.

Scott, Kevin R., et al., "Dementia Syndromes: Evaluation and Treatment", Expert Rev. Neurotherapeutics 7 (4), (2007), 407-422.

Sheldrick, George M., "Phase Annealing in SHELX-90: Direct Methods for Larger Structures", Acta Cryst. A46, (1990), 467-473.

"International Application Serial No. PCT/GB2009/051135, International Search Report and Written Opinion mailed Nov. 25, 2009", 14 pgs.

"International Application Serial No. PCT/GB2009/051136, International Search Report and Written Opinion mailed Nov. 26, 2009", 14 pgs.

Kenney, Christopher, et al., "Tetrabenazine in the treatment of hyperkinetic movement disorders", Expert Rev. Neurotherapeutics 6(1), (2006), 7-17.

Ligeiro De Oliveira, A.P., "Effects of single or repeated amphetamine treatment and withdrawl on lung allergic inflammation in rats", International immunopharmacology vol. 8, (2008), 1164-1171.

"A novel gene containing a trinucleotide repeat that is expanded and unstable on Huntington's disease chromosomes. The Huntington's Disease Collaborative Research Group.", Cell, 72(6), [No authors listed], (Mar. 26, 1993), 971-83.

"U.S. Appl. No. 12/997,258, Preliminary Amendment filed Dec. 10, 2010", 5 pgs.

Aparicio-Legarza, Iraide M, et al., "Deficits of [3H]D-aspartate binding to glutamate uptake sites in striatal and accumbens tissue in patients with schizophrenia", Neurosci Lett., 232(1), (Aug. 22, 1997), 13-6.

Benjamin, C. M, et al., "Proceed with care: direct predictive testing for Huntington disease.", Am J Hum Genet., 55(4), (Oct. 1994), 606-17.

Bennett, Frank C, et al., "An ICAM-1 antisense oligonucleotide prevents and reverses dextran sulfate sodium-induced colitis in mice", J Pharmacol Exp Ther., 280(2), (Feb. 1997), 988-1000.

Berthois, Y., et al., "SR31747A is a sigma receptor ligand exhibiting antitumoural activity both in vitro and in vivo", Br J Cancer., 88(3), (Feb. 10, 2003), 438-46.

Bevan, S, et al., "Development of a Competitive Antagonist for the Sensory Neurone Excitant Capsaicn", British Journal of Pharmacology: Proceedings Supplement, [Online]. Retrieved from the Internet: <URL: http://wwwpA2online.org/vol_12issue4-abst077P.html>, (Dec. 1990), 23 pgs.

Bonhaus, D. W, et al., "The pharmacology and distribution of human 5-hydroxytryptamine2B (5-HT2B) receptor gene products: comparison with 5-HT2A and 5-HT2C receptors.", Br J Pharmacol., 115(4), (Jun. 1995), 622-8.

Brent, P. J, et al., "Sigma binding site ligands inhibit cell proliferation in mammary and colon carcinoma cell lines and melanoma cells in culture.", Eur J Pharmacol., 278(2), (May 15, 1995), 151-60.

Brinkman, R R, et al., "The likelihood of being affected with Huntington disease by a particular age, for a specific CAG size", Am J Hum Genet., 60(5), (May 1997), 1202-10.

Brown, C. M, et al., "Alpha 2-adrenoceptor subtypes and imidazoline-like binding sites in the rat brain.", Br J Pharmacol., 99(4), (Apr. 1990), 803-9.

Crawford, K. W, et al., "Sigma-2 receptor agonists activate a novel apoptotic pathway and potentiate antineoplastic drugs in breast tumor cell lines", Cancer Res., 62(1), (Jan. 1, 2002), 313-22.

Erickson, J. D, et al., "Distinct pharmacological properties and distribution in neurons and endocrine cells of two isoforms of the human vesicular monoamine transporter.", Proc Natl Acad Sci U S A., 93(10), (May 14, 1996), 5166-71.

Ganapathy, Malliga E, et al., "Molecular and ligand-binding characterization of the sigma-receptor in the Jurkat human T lymphocyte cell line", J Pharmacol Exp Ther., 289(1), (Apr. 1999), 251-60.

Grayson, B, et al., "The Effect of PCP on Novel Object Recognition in the Rat", Journal of Psychopharmacology vol. 18, No. 3, Supplement, (2004), A55.

Grayson, B., et al., "Atypical antipsychotics attenuate a sub-chronic PCP-induced cognitive deficit in the novel object recognition task in the rat.", Behav Brain Res., 184(1), (Nov. 22, 2007), 31-8.

Gu, H., et al., "Stable expression of biogenic amine transporters reveals differences in inhibitor sensitivity, kinetics, and ion dependence", J Biol Chem., 269(10), (Ma. 11, 1994), 7124-30.

Halloran, Margaret M, et al., "Cellular adhesion molecules in rat adjuvant arthritis.", Arthritis Rheum., 39(5), (May 1996), 810-9.

Hanner, Markus, et al., "Purification, molecular cloning, and expression of the mammalian sigma1-binding site", Proc Natl Acad Sci U S A., 93(15), (Jul. 23, 1996), 8072-7.

Hashimoto, Kenji, et al., "Further characterization of [3H]ifenprodil binding to sigma receptors in rat brain.", European Journal of Pharmacology, 236(1), (May 12, 1993), 159-163.

Hensiek, A. E, et al., "Relevance of new psychotropic drugs for the neurologist", J Neurol Neurosurg Psychiatry, 72(3), (Mar. 2002), 281-5.

Huttunen, Matti, et al., "The evolution of the serotonin-dopamine antagonist concept", J Clin Psychopharmacol., 15(1 Suppl 1), (Feb. 1995), 4S-10S.

Idris, N. F, et al., "The ability of antipsychotics to prevent a subchronic PCP-induced cognitive deficit in the novel oject recognition task in the rat", Neuroscience 2005 Abstract: Presentation No. 67.15, (2005), 1 pg.

Jentsch, David J, et al., "The neuropsychopharmacology of phencyclidine: from NMDA receptor hypofunction to the dopamine hypothesis of schizophrenia.", Neuropsychopharmacology, 20(3), (Mar. 1999), 201-25.

Karpuj, Marcela V, et al., "Prolonged survival and decreased abnormal movements in transgenic model of Huntington disease, with administration of the transglutaminase inhibitor cystamine.", Nat Med., 8(2), (Feb. 2002), 143-9.

Knoerzer, Debbie Barney, et al., "Clinical and histological assessment of collagen-induced arthritis progression in the diabetes-resistant BB/Wor rat", Toxicol Pathol., 25(1), (Jan.-Feb. 1997), 13-9.

Meltzer, Herbert, "The role of serotonin in schizophrenia and the place of serotonin-dopamine antagonist antipsychotics", J Clin Psychopharmacol., 15(1 Suppl 1), (Feb. 1995), 2S-3S.

Millan, M. J, et al., "Specific labelling of serotonin 5-HT(1B) receptors in rat frontal cortex with the novel, phenylpiperazine derivative, [3H]GR125,743. A pharmacological characterization", Pharmacol Biochem Behav., 71(4), (Apr. 2002), 589-98.

Mosharov, Eugene V, et al., "Intracellular patch electrochemistry: regulation of cytosolic catecholamines in chromaffin cells", J Neurosci., 23(13), (Jul. 2, 2003), 5835-45.

Near, Joseph, et al., "[3H]Dihydrotetrabenazine binding to bovine striatal synaptic vesicles.", Mol Pharmacol., 30(3), (Sep. 1986), 252-7.

Nociari, M, et al., "A novel one-step, highly sensitive fluorometric assay to evaluate cell-mediated cytotoxicity", Journal of Immunological Methods 213(2), (Jun. 1998), 157-167.

Oppenheimer-Marks, N, et al., "Interleukin 15 is produced by endothelial cells and increases the transendothelial migration of T cells in vitro and in the SCID mouse-human rheumatoid arthritis model In vivo.", J Clin Invest., 101(6), (Mar. 15, 1998), 1261-72.

Scherman, Daniel, et al., "[3H]dihydrotetrabenazine, a new in vitro monoaminergic probe for human brain", J Neurochem., 50(4), (Apr. 1998), 1131-6.

Schimmer, Ralph C, et al., "Streptococcal cell wall-induced arthritis: requirements for IL-4, IL-10, IFN-gamma, and monocyte chemoattractant protein-1", J Immunol., 160(3), (Feb. 1, 1998), 1466-71.

Spruce, Barbara A, et al., "Small molecule antagonists of the sigma-1 receptor cause selective release of the death program in tumor and self-reliant cells and inhibit tumor growth in vitro and in vivo.", Cancer Res., 64(14), (Jul. 15, 2004), 4875-86.

Staal, R. G, et al., "In vitro studies of striatal vesicles containing the vesicular monoamine transporter (VMAT2): rat versus mouse differences in sequestration of 1-methyl-4-phenylpyridinium.", J Pharmacol Exp Ther., 293(2), (May 2000), 329-35.

Sutcliffe, J S, et al., "A preliminary investigation into the effects of gender on cognitive performance in the rat using the novel object recognition task", Endocrine Abstracts, 10, Presented at the 196th meeting of the Society for Endocrinology, (2005), P50.

Uhlen, S., et al., "The novel alpha-2 adrenergic radioligand [3H]-MK912 is alpha-2C selective among human alpha-2A, alpha-2B and alpha-2C adrenoceptors.", J Pharmacol Exp Ther., 271(3), (Dec. 1994), 1558-65.

Uhlen, Staffan, "[3H]RS79948-197 binding to human, rat, guinea pig and pig a2A-, a2B- and a2C-adrenoceptors. Comparison with MK912, RX821002, rauwolscine and yohimbine", European Journal of Pharmacology 343(1), (1998), 93-101.

Wang, B., et al., "Expression of sigma 1 receptor in human breast cancer", Breast Cancer Res Treat., 87(3), (Oct. 2004), 205-14.

Zucker, M., et al., "Characterization of high-affinity [3H]TBZOH binding to the human platelet vesicular monoamine transporter", Life Sci., 69(19), (Sep. 28, 2001), 2311-7.

"U.S. Appl. No. 10/597,803, Non Final Office Action mailed Jan. 29, 2009", 9 pgs.

"U.S. Appl. No. 10/597,803, Preliminary Amendment filed Aug. 8, 2006", 7 pgs.

"U.S. Appl. No. 10/597,803, Response filed Apr. 26, 2010 to Final Office Action mailed Oct. 27, 2009", 24 pgs.

"U.S. Appl. No. 10/597,803, Response filed Dec. 24, 2008 to Restriction Requirement mailed Sep. 30, 2008", 7 pgs.

"U.S. Appl. No. 10/597,803, Restriction Requirement mailed Sep. 30, 2008", 9 pgs.

"U.S. Appl. No. 12/555,695, Amendment under 37 CFR 1.312 filed Nov. 16, 2010", 8 pgs.

"International Application Serial No. PCTGB2009051013, International Search Report and Written Opinion mailed Oct. 8, 2010", 14 pgs.

Abrahamsson, Bertil, et al., "Absorption, Gastrointestinal Transit, and Tablet Erosion of Felodipine Extended-Release (ER) Tablets", Pharmaceutical Research 10(5), (1993), 709-714.

Colorcon Limitied, "The Effect of In-Vitro Dissolution Parameters on the Release Rate of a Low Dose, Low Solubility Drug from Extended Release Hypromellose Matrix Formulations", Poster Reprint, Controlled Release Society, (Jul. 2006), 4 pgs.

Wingstrand, Karin, et al., "Bioavailability from felodipine extended-release tablets with different dissolution properties", International Journal of Pharmaceutics 60, (1990), 151-156.

PHARMACEUTICAL COMPOUNDS

RELATED APPLICATIONS

This application claims benefit of the filing date of UK Patent Application No. 0816371.9 filed Sep. 8, 2008, the contents of which are specifically incorporated herein in their entirety.

FIELD OF THE INVENTION

This invention relates to use of dihydrotetrabenazines for the treatment of dementia.

BACKGROUND OF THE INVENTION

Dementia is a progressive disorder characterised by memory loss and impaired cognitive ability. It has been defined as a decline in memory with impairment of at least one other cognitive function, such as skilled movements (limb apraxia), language (aphasia) or executive function (e.g. planning, attention and abstract reasoning). The decline appears as a noticeable change in behaviour and typically impairs social and/or occupational functioning. The condition is distinct from memory loss and cognitive decline associated with other psychiatric conditions such as depression, mood disorders or psychosis.

Dementia comes in many forms and has many causes. The most common forms of dementia are dementia associated with Alzheimer's disease, Lewy body dementia and vascular dementia arising from cerebrovascular injuries such as stroke.

Alzheimer's disease is by far the most common type of dementia and is estimated to account for 60% to 80% of all cases. Patients suffering from Alzheimer's disease typically initially experience insidious memory loss and focal cognitive dysfunction. This is followed by progressive deterioration of cortical functions such as language, visuospatial tasks, abstract reasoning, calculating, left-right disorientation and/or limb praxis. Motor skills such as walking are generally preserved. The onset of Alzheimer's disease typically occurs after 45 years of age but is more common after 65 years of age.

Alzheimer's disease is determined by clinical diagnosis. There is currently no definitive laboratory test that can be carried out on a live patient which can confirm the presence of the condition, although brain imaging such as tomography or magnetic resonance imaging can contribute towards a diagnosis.

Alzheimer's disease is characterised by loss of neurons and synapses in the cerebral cortex and certain subcortical regions. This loss results in atrophy of the affected regions, including degeneration in the temporal lobe and parietal lobe, and parts of the frontal cortex and cingulate gyrus. The disease is associated with the accumulation of neuritic plaques (amyloid plaques) and neurofibrillary tangles in the brain. The amyloid plaques are made up from amyloid-β, small peptides 39-43 amino acids in length that are fragments of a larger protein amyloid precursor protein (APP), a transmembrane protein that penetrates through the neuron's membrane. APP is critical to neuron growth, survival and post-injury repair but, in Alzheimer's disease, an unknown process causes APP to be divided into smaller fragments, one of which consists of amyloid-β fibrils. The amyloid-β fibrils form clumps that deposit around the neurons in dense formations as plaques. The neurofibrillary tangles are caused by hyperphosphorylation of tau protein.

Lewy body disease, a synucleinopathy, is second only to Alzheimer's disease in prevalence and symptoms include deficits in attention and concentration, reduced verbal fluency, difficulty in performing visuospatial tasks and psychomotor slowing, as well as parkinsonism. The disease is characterised by the accumulation of insoluble neuronal inclusions known as Lewy Bodies, formed predominantly from insoluble α-synuclein, in the cortical and subcortical regions of affected individuals.

Vascular dementias account for about 10-20% of dementia cases and typically arise as a consequence of a cerebrovascular disease resulting in stroke(s).

Other forms of dementia include those associated with or arising from tauopathies such as Pick's disease and prionopathies such as Creutzfeldt-Jakob disease and new variant Creutzfeldt-Jakob disease.

Further information on the various types of dementia may be found in the reviews by Bradley F. Boeve, "*A Review of the Non-Alzheimer's Dementias, J. Clin. Psychiatry,* 2006; 67: 1985-2001 and Kevin R. Scott et al., "*Dementia syndromes: evaluation and treatment*", *Expert Rev. Neurotherapeutics* 7 (4), 2007, 407-422 and references cited therein.

SUMMARY OF THE INVENTION

The present invention relates to the use of the above-mentioned 3,11b cis-dihydrotetrabenazine isomers in the treatment of dementia and cognitive deficit symptoms of dementia.

Therefore, one aspect of the invention is a method of treating dementia or a cognitive deficit associated with dementia in a patient in need thereof, which method includes administering to the patient a therapeutically effective amount of a 3,11b-cis-dihydrotetrabenazine or a pharmaceutically acceptable salt thereof, to thereby treat dementia or a cognitive deficit associated with dementia in the patient.

For example, wherein the 3,11b-cis-dihydrotetrabenazine, or a pharmaceutically acceptable salt thereof, can be a 2S,3S, 11bR isomer of 3,11b-cis-dihydrotetrabenazine having the formula (Ia):

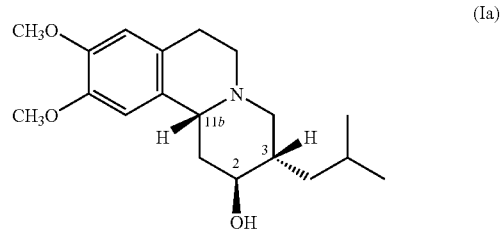

(Ia)

or a pharmaceutically acceptable salt thereof.

In other embodiments, the 3,11b-cis-dihydrotetrabenazine, or a pharmaceutically acceptable salt thereof, can be a 2R,3R,11bS isomer of 3,11b-cis-dihydrotetrabenazine having the formula (Ib):

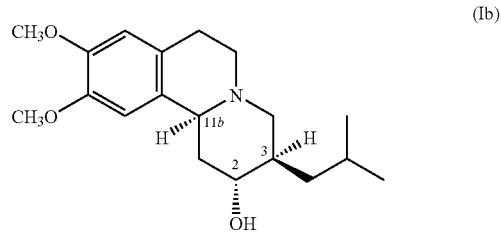

(Ib)

or a pharmaceutically acceptable salt thereof.

In further embodiments, the 3,11b-cis-dihydrotetrabenazine, or a pharmaceutically acceptable salt thereof, can be a 2R,3S,11bR isomer of 3,11b-cis-dihydrotetrabenazine having the formula (Ic):

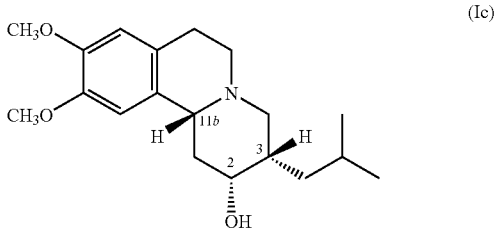

(Ic)

or a pharmaceutically acceptable salt thereof.

In additional embodiments, the 3,11b-cis-dihydrotetrabenazine, or a pharmaceutically acceptable salt thereof, can be a 2S,3R,11bS isomer of 3,11b-cis-dihydrotetrabenazine having the formula (Id):

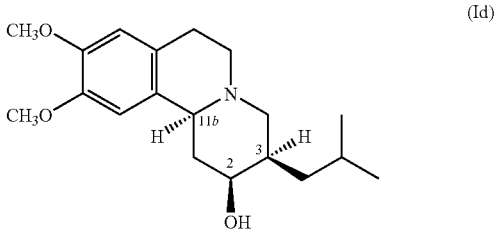

(Id)

or a pharmaceutically acceptable salt thereof.

In some formulations and methods of the 3,11b-cis-dihydrotetrabenazine is a free base. In other formulations and methods the pharmaceutically acceptable salt of 3,11b-cis-dihydrotetrabenazine is an acid addition salt. For example, the salt can be a methane sulphonate salt.

As described herein the dementia can be any dementia. Examples include dementia such as: (a) Alzheimer's disease; (b) Lewy body dementia; and/or (c) Vascular dementia. The dementia can arise from or be associated with: (a) accumulation of amyloid plaques in the brain; and/or (b) development of neurofibrillary tangles in the brain; and/or (c) accumulation of Lewy bodies in the brain: and/or (d) cerebrovascular injury in the brain. Moreover, the dementia can be a form of dementia arising from: (a) an amyloidopathy; and/or (b) a tauopathy; and/or (c) a synucleinopathy; and/or (d) a prionopathy. In some embodiments, a cognitive deficit associated with dementia is treated.

Another aspect of the invention is 3,11b cis-dihydrotetrabenazine or a pharmaceutically acceptable salt thereof for use in the treatment of dementia.

Another aspect of the invention is the use of a 3,11b cis-dihydrotetrabenazine or a pharmaceutically acceptable salt thereof for the manufacture of a medicament for the treatment of dementia.

In a further aspect, the invention provides a method of treating dementia in a patient suffering therefrom, which method comprises administering to the patient a therapeutically effective amount of a 3,11b cis-dihydrotetrabenazine or a pharmaceutically acceptable salt thereof.

DETAILED DESCRIPTION OF THE INVENTION

Figure 1:
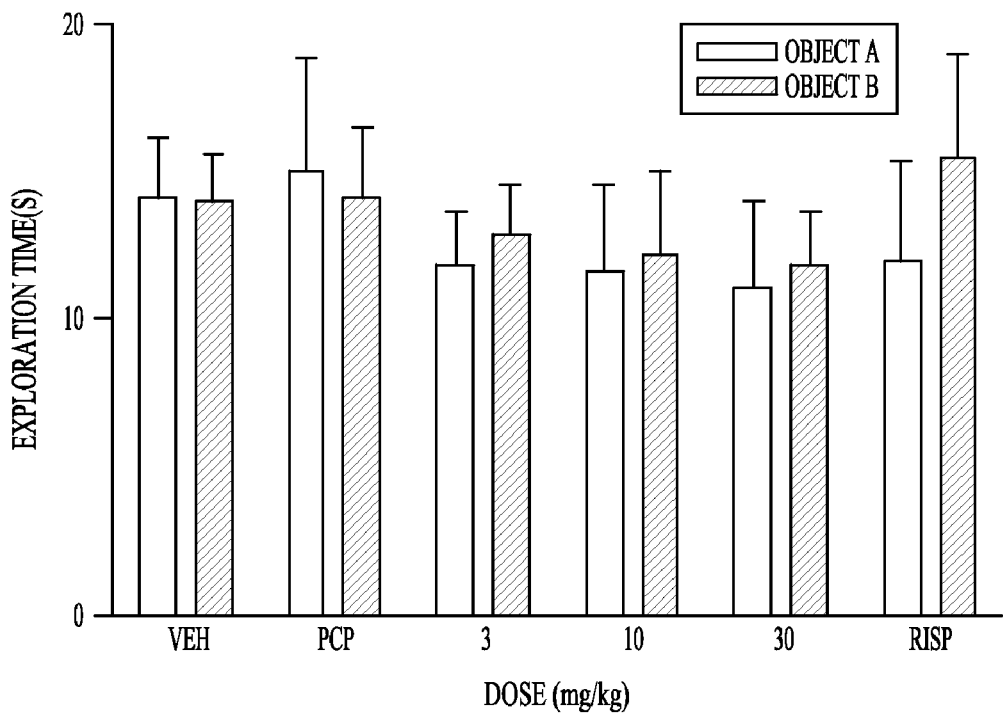
FIG. 1 illustrates the mean exploration time of identical objects in the acquisition phase-T1—following acute administration of Isomer A (3.0-30 mg/kg, p.o. (orally)) and risperidone (Risp 0.2 mg/kg, i.p (intraperitoneally)) in sub-chronic phencyclidine hydrochloride (PCP) (2 mg/kg, i.p twice daily for seven days) and vehicle treated rats.

As described and illustrated herein, 3,11b-cis-dihydrotetrabenazine is useful for treatment of dementia and the symptoms of dementia. Accordingly, one aspect of the invention is a method of treating dementia in a patient that includes administering to the patient a therapeutically effective amount of a 3,11b cis-dihydrotetrabenazine, an isomer thereof and/or a pharmaceutically acceptable salt thereof.

The terms "treatment" and "treating" are used herein in a general sense to mean a therapeutic intervention that results in a positive effect on one or more symptoms or aspects of dementia or the progression of the disease. Thus, treatment may result in the progression of the disease being slowed, halted, or even reversed. Alternatively, or additionally, treatment may result in one or more symptoms being improved or the severity or frequency of the symptoms being reduced, or the rate of deterioration (in terms of the severity or frequency of the symptoms) being slowed down.

International application WO 2005/077946 (specifically incorporated herein by reference in its entirety) discloses the preparation of 3,11b cis-dihydrotetrabenazine isomers and their use in a range of movement disorders. International patent application WO 2007/017654 (specifically incorporated herein by reference in its entirety) discloses the use of 3,11b cis-dihydrotetrabenazines for treating schizophrenia and other psychoses. Example 6 of WO 2007/017654 describes studies carried out to investigate the effect of Isomer (Ib) above on cognitive deficit in patients suffering from schizophrenia. Moreover, International application WO 2007/007105 (specifically incorporated herein by reference in its entirety) discloses the use of 3,11b cis-dihydrotetrabenazines for preventing or reducing the development or progression of the symptoms of Huntington's disease. Example 5 in WO 2007/007105 describes the effect of a 3,11b cis-dihydrotetrabenazine isomer in a transgenic mouse model of Huntington's disease.

There are four isomers of 3,11b cis-dihydrotetrabenazine. Any one of these isomers, or a combination thereof, can be used in the methods and compositions described herein. These 3,11b cis-dihydrotetrabenazine isomers are the 2S,3S, 11bR isomer, the 2R,3R,11bS isomer, the 2R,3S,11bR isomer and the 2S,3R,11bS isomer, which have the following structures:

(a) the 2S,3S,11bR isomer of 3,11b-cis-dihydrotetrabenazine having the formula (Ia):

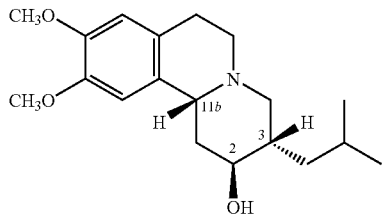

(b) the 2R,3R,11bS isomer of 3,11b-cis-dihydrotetrabenazine having the formula (Ib):

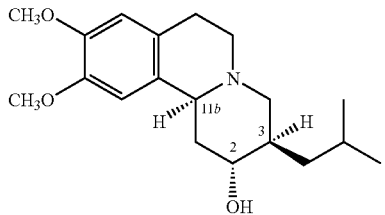

(c) the 2R,3S,11bR isomer of 3,11b-cis-dihydrotetrabenazine having the formula (Ic):

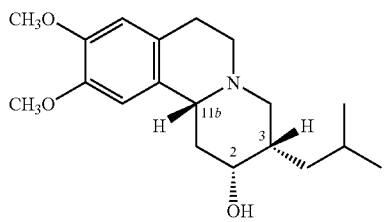

and (d) the 2S,3R,11bS isomer of 3,11b-cis-dihydrotetrabenazine having the formula (Id):

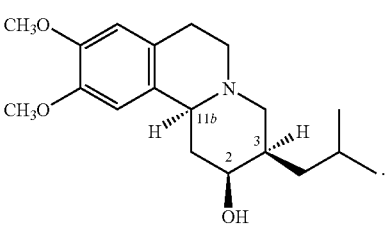

In some embodiments, the isomer employed in the methods and compositions is the 3,11b-cis-dihydrotetrabenazine of the formula (Ib):

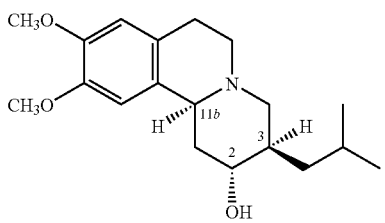

or a pharmaceutically acceptable salt thereof.

The individual isomers of the invention can be characterised by their spectroscopic, optical and chromatographic properties, and also by their absolute stereochemical configurations as determined by X-ray crystallography.

The four 3,11b cis-dihydrotetrabenazine isomers may be characterised as follows:

Isomer A

Optical activity as measured by optical rotatory dispersion (ORD; methanol, 21° C.) as laevorotatory (−), infrared (IR) analysis (KBr solid), nuclear magnetic resonance (NMR), particularly $^{1}$H-NMR (CDCl$_{3}$) and/or $^{13}$C-NMR (CDCl$_{3}$) analysis substantially as described in Table 1. Isomer A corresponds to formula (Ib) above.

Isomer B

Optical activity as measured by ORD (methanol, 21° C.) as dextrorotatory (+), IR (KBr solid) analysis and NMR, particularly $^{1}$H-NMR (CDCl$_{3}$) and $^{13}$C-NMR (CDCl$_{3}$), analysis, substantially as described in Table 1, as well as X-ray crystallographic properties as described in Example 4. Isomer B corresponds to formula (Ia) above.

Isomer C

Optical activity as measured by ORD (methanol, 21° C.) as dextrorotatory (+), IR (KBr solid) analysis, and NMR, particularly $^{1}$H-NMR (CDCl$_{3}$) and $^{13}$C-NMR (CDCl$_{3}$) analysis, substantially as described in Table 2. Isomer C corresponds to either formula (Ic) or (Id) above.

Isomer D

Optical activity as measured by ORD (methanol, 21° C.) as laevorotatory (−), IR (KBr solid) analysis, NMR, particularly $^{1}$H-NMR (CDCl$_{3}$) and $^{13}$C-NMR (CDCl$_{3}$) analysis, substantially as described in Table 2. Isomer D corresponds to either formula (Ic) or formula (Id) above.

ORD values for each isomer are given in the examples below but it is noted that such values are given by way of example and may vary according to the degree of purity of the isomer and the influence of other variables such as temperature fluctuations and the effects of residual solvent molecules.

The isomers A, B, C and D may each be presented in a substantially enantiomerically pure form or as mixtures with other 3,11b cis-dihydrotetrabenazine isomers.

The 3,11b-cis-dihydrotetrabenazine used in the invention may be in substantially pure form, for example at an isomeric purity of greater than 90%, typically greater than 95% and more preferably greater than 98%.

The term "isomeric purity" in the present context refers to the amount of a particular 3,11b-cis-dihydrotetrabenazine isomer present relative to the total amount or concentration of dihydrotetrabenazine of all isomeric forms. For example, if 90% of the total dihydrotetrabenazine present in the composition is 3,11b-cis-dihydrotetrabenazine Isomer A, then the isomeric purity is 90%.

The terms "enantiomeric purity" and "enantiomerically pure" in the present context refer to the amount of a given 3,11b-cis-dihydrotetrabenazine isomer present relative to the total amount or concentration of dihydrotetrabenazine of all enantiomeric and isomeric forms. For example, if 90% of the total dihydrotetrabenazine present in the composition is in the form of a single enantiomer, then the enantiomeric purity is 90%.

By way of example, in each aspect and embodiment of the invention, the 3,11b-cis-dihydrotetrabenazine may be present in an enantiomeric purity of at least 55% (e.g. at least 60%, 65%, 70%, 75%, 80%, 85%, 90%, 95%, 97%, 98%, 99%, 99.5% or 100%).

Alternatively, the 3,11b-cis-dihydrotetrabenazine may also be presented in the form of mixtures with one or more of Isomers A, B, C and D. Such mixtures may be racemic mixtures or non-racemic mixtures. Examples of racemic mixtures include the racemic mixture of Isomer A and Isomer B.

The dementia treated according to the invention may be a form of dementia selected from: (a) Alzheimer's disease; (b) Lewy body dementia; and (c)Vascular dementia.

The dementia may be one arising from or associated with: (a) the accumulation of amyloid plaques in the brain; and/or (b) the development of neurofibrillary tangles in the brain; and/or (c) the accumulation of Lewy bodies in the brain and/or; (d) the accumulation of cerebrovascular injury in the brain.

Alternatively, or additionally, the dementia may be a form of dementia arising from:
(a) an amyloidopathy; and/or (b) a tauopathy; and/or (c) a synucleinopathy; and/or
(d) a prionopathy.

In some embodiments, the 3,11b-cis-dihydrotetrabenazine is used to treat a cognitive deficit associated with dementia.

Accordingly, the invention also provides:
A 3,11b-cis-dihydrotetrabenazine (e.g. any one or more of the 2S,3S,11bR isomer, the 2R,3R,11bS isomer, the 2R,3S,11bR isomer and the 2S,3R,11bS isomer), or a pharmaceutically acceptable salt thereof, for use in treating dementia and/or a cognitive deficit associated with dementia.

The use of a 3,11b-cis-dihydrotetrabenazine (e.g. any one or more of the 2S,3S,11bR isomer, the 2R,3R,11bS isomer, the 2R,3S,11bR isomer and the 2S,3R,11bS isomer), or a pharmaceutically acceptable salt thereof, for the manufacture of a medicament for treating a cognitive deficit associated with dementia.

A method of treating dementia and/or a cognitive deficit associated with dementia in a patient in need thereof, which method comprises administering to the patient a therapeutically effective amount of a 3,11b-cis-dihydrotetrabenazine (e.g. any one or more of the 2S,3S, 11bR isomer, the 2R,3R,11bS isomer, the 2R,3S,11bR isomer and the 2S,3R,11bS isomer) or a pharmaceutically acceptable salt thereof.

Figure 2:
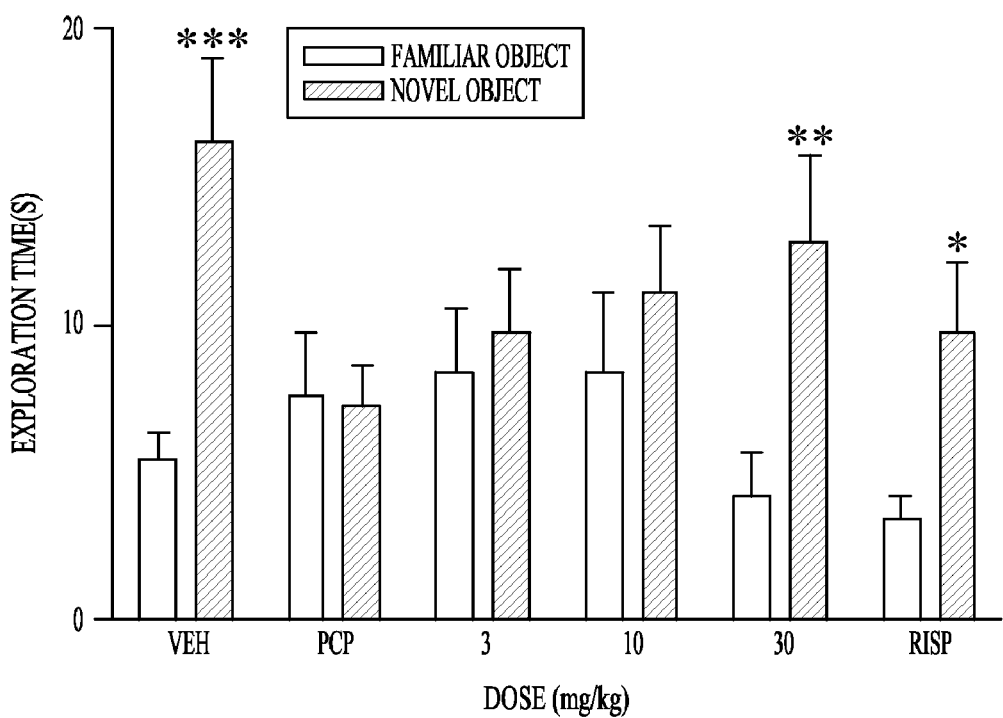
FIG. 2 illustrates the ability of acute Isomer A (3-30 mg/kg, p.o) and risperidone (Risp 0.2 mg/kg, i.p) to attenuate the effect of sub-chronic PCP on the exploration time (s) of a familiar object and a novel object in a 3 minute retention trial in female hL rats. Significant difference between time spent exploring the familiar and novel object *P<0.05–***P<0.001.

For example, acute treatment of rats with Isomer A counteracted the effects of sub-chronic administration of phencyclidine hydrochloride (PCP) rats during novel object recognition (NOR) testing by generally improving the working memory deficits induced by PCP (see Examples and FIG. 2).

Pharmaceutically Acceptable Salts

Unless the context requires otherwise, a reference in this application to 3,11b-cis-dihydrotetrabenazine and its isomers includes within its scope not only the free base of the dihydrotetrabenazine but also its salts. One example of a pharmaceutically acceptable dihydrotetrabenazine salt is an acid addition salt of dihydrotetrabenazine.

Particular acids from which the acid addition salts are formed include acids having a pKa value of less than 3.5 and more usually less than 3. For example, the acid addition salts can be formed from an acid having a pKa in the range from +3.5 to −3.5.

Preferred acid addition salts include those formed with sulphonic acids such as methanesulphonic acid, ethanesulphonic acid, benzene sulphonic acid, toluene sulphonic acid, camphor sulphonic acid and naphthalene sulphonic acid.

One example of an acid from which acid addition salts may be formed is methanesulphonic acid.

Acid addition salts can be prepared by the methods described herein or conventional chemical methods such as the methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free base form of the compound with the appropriate base or acid in water, or in an organic solvent, or in a mixture of the two. In some embodiments, a non-aqueous media is employed such as ether, ethyl acetate, ethanol, isopropanol, or acetonitrile.

The salts are typically pharmaceutically acceptable salts. However, salts that are not pharmaceutically acceptable may also be prepared as intermediate forms which may then be converted into pharmaceutically acceptable salts. Such non-pharmaceutically acceptable salt forms also form part of the invention.

Methods for the Preparation of Dihydrotetrabenazine Isomers

The dihydrotetrabenazines of the invention can be prepared by the methods described in WO 2005/077946 and WO 2007/017654, the contents of which are incorporated herein by reference, and in the examples set forth below.

Pharmaceutical Formulations

The 3,11b-cis-dihydrotetrabenazine is typically administered in the form of a pharmaceutical composition.

The pharmaceutical compositions can be in any form suitable for oral, parenteral, topical, intranasal, intrabronchial, ophthalmic, optic, rectal, intra-vaginal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery.

Pharmaceutical dosage forms suitable for oral administration include tablets, capsules, caplets, pills, lozenges, syrups, solutions, sprays, powders, granules, elixirs and suspensions, sublingual tablets, sprays, wafers or patches and buccal patches.

Pharmaceutical compositions containing the 3,11b-cis-dihydrotetrabenazine can be formulated in accordance with known techniques, see for example, Remington's Pharmaceutical Sciences, Mack Publishing Company, Easton, Pa., USA.

Thus, tablet compositions can contain a unit dosage of active compound together with an inert diluent or carrier such as a sugar or sugar alcohol, e.g.; lactose, sucrose, sorbitol or mannitol; and/or a non-sugar derived diluent such as sodium carbonate, calcium phosphate, talc, calcium carbonate, or a cellulose or derivative thereof such as methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Capsule formulations may be of the hard gelatin or soft gelatin variety and can contain the active component in solid, semi-solid, or liquid form. Gelatin capsules can be formed from animal gelatin or synthetic or plant derived equivalents thereof.

The solid dosage forms (e.g.; tablets, capsules etc.) can be coated or un-coated, but typically have a coating, for example a protective film coating (e.g. a wax or varnish) or a release controlling coating. The coating (e.g. a Eudragit™ type polymer) can be designed to release the active component at a desired location within the gastro-intestinal tract. Thus, the coating can be selected so as to degrade under certain pH conditions within the gastrointestinal tract, thereby selectively release the compound in the stomach or in the ileum or duodenum.

Instead of, or in addition to, a coating, the drug can be presented in a solid matrix comprising a release controlling agent, for example a release delaying agent that may be adapted to selectively release the compound under conditions of varying acidity or alkalinity in the gastrointestinal tract. Alternatively, the matrix material or release retarding coating can take the form of an erodible polymer (e.g. a maleic anhydride polymer) which is substantially continuously eroded as the dosage form passes through the gastrointestinal tract.

Compositions for topical use include ointments, creams, sprays, patches, gels, liquid drops and inserts (for example, intraocular inserts). Such compositions can be formulated in accordance with known methods.

Compositions for parenteral administration are typically presented as sterile aqueous or oily solutions or fine suspensions, or may be provided in finely divided sterile powder form for making up extemporaneously with sterile water for injection.

Examples of formulations for rectal or intra-vaginal administration include pessaries and suppositories which may be, for example, formed from a shaped mouldable or waxy material containing the active compound.

Compositions for administration by inhalation may take the form of inhalable powder compositions or liquid or powder sprays, and can be administrated in standard form using powder inhaler devices or aerosol dispensing devices. Such devices are well known. For administration by inhalation, the powdered formulations typically comprise the active compound together with an inert solid powdered diluent such as lactose.

The compound of the invention will generally be presented in unit dosage form and, as such, will typically contain sufficient compound to provide a desired level of biological activity. For example, a formulation intended for oral administration may contain from 2 milligrams to 200 milligrams of active ingredient, more usually from 10 milligrams to 100 milligrams, for example, 12.5 milligrams, 25 milligrams and 50 milligrams.

Methods of Treatment

The 3,11b-cis-dihydrotetrabenazine will be administered to a patient in need thereof (for example a human or animal patient) in an amount sufficient to achieve the desired therapeutic effect.

The patient in need of such administration is a patient suffering from, or suspected of suffering from, one or more forms of dementia (see discussion herein, including the Examples).

The desired effect can be the prevention, alleviation or reduction of the severity of the dementia or one or more symptoms thereof. Such symptoms are well known to the skilled person (e.g. a skilled physician) who will be able to judge through clinical evaluation and testing in a conventional manner whether or not the administration of a compound of the invention has resulted in a change in the symptoms exhibited by the patient.

The compound can be administered in amounts that are therapeutically or prophylactically useful and which generally are non-toxic. However, in certain situations, the benefits of administering the 3,11b-cis-dihydrotetrabenazine may outweigh the disadvantages of any toxic effects or side effects, in which case it may be considered desirable to administer compounds in amounts that are associated with a degree of toxicity.

A typical daily dose of the compound can be up to 1000 mg per day, for example in the range from 0.01 milligrams to 10 milligrams per kilogram of body weight, more usually from 0.025 milligrams to 5 milligrams per kilogram of body weight, for example up to 3 milligrams per kilogram of body-weight, and more typically 0.15 milligrams to 5 milligrams per kilogram of bodyweight although higher or lower doses may be administered where required.

Ultimately, however, the quantity of compound administered will be commensurate with the nature of the disease or physiological condition being treated and the therapeutic benefits and the presence or absence of side effects produced by a given dosage regimen, and will be at the discretion of the physician.

EXAMPLES

The following non-limiting examples illustrate the synthesis and properties of the 3,11b-cis-dihydrotetrabenazine isomers.

Example 1

Preparation of 2S,3S,11bR and 2R,3R,11bS Isomers of Dihydrotetrabenazine

1A. Reduction of RR/SS Tetrabenazine

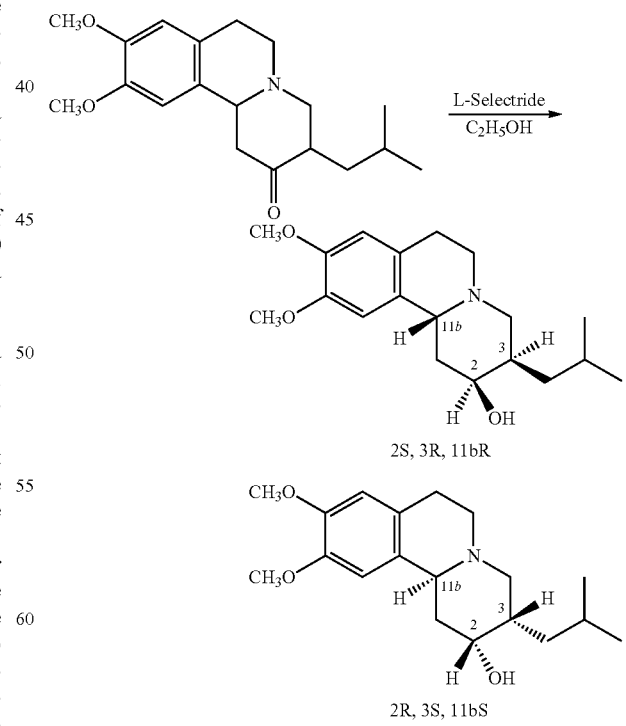

1M L-Selectride® in tetrahydrofuran (135 ml, 135 mmol, 2.87 eq.) was added slowly over 30 minutes to a stirred solution of tetrabenazine RR/SS racemate (15 g, 47 mmol) in ethanol (75 ml) and tetrahydrofuran (75 ml) at 0° C. After addition was complete the mixture was stirred at 0° C. for 30 minutes and then allowed to warm to room temperature.

The mixture was poured onto crushed ice (300 g) and water (100 ml) added. The solution was extracted with diethyl ether (2×200 ml) and the combined ethereal extracts washed with water (100 ml) and partly dried over anhydrous potassium carbonate. Drying was completed using anhydrous magnesium sulphate and, after filtration, the solvent was removed at reduced pressure (shielded from the light, bath temperature <20° C.) to afford a pale yellow solid.

The solid was slurried with petroleum ether (30-40° C.) and filtered to afford a white powdery solid (12 g, 80%).

1B. Dehydration of Reduced Tetrabenazine purified by column chromatography (silica, ethyl acetate) to afford the semi-pure alkene as a yellow solid (10.87 g, 58%).

1C. Hydration of the Crude Alkene from Example 1B

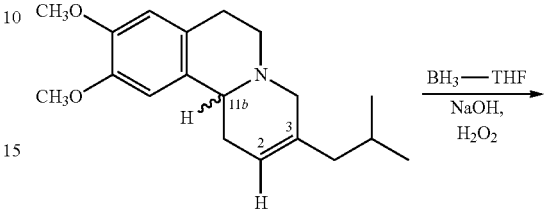

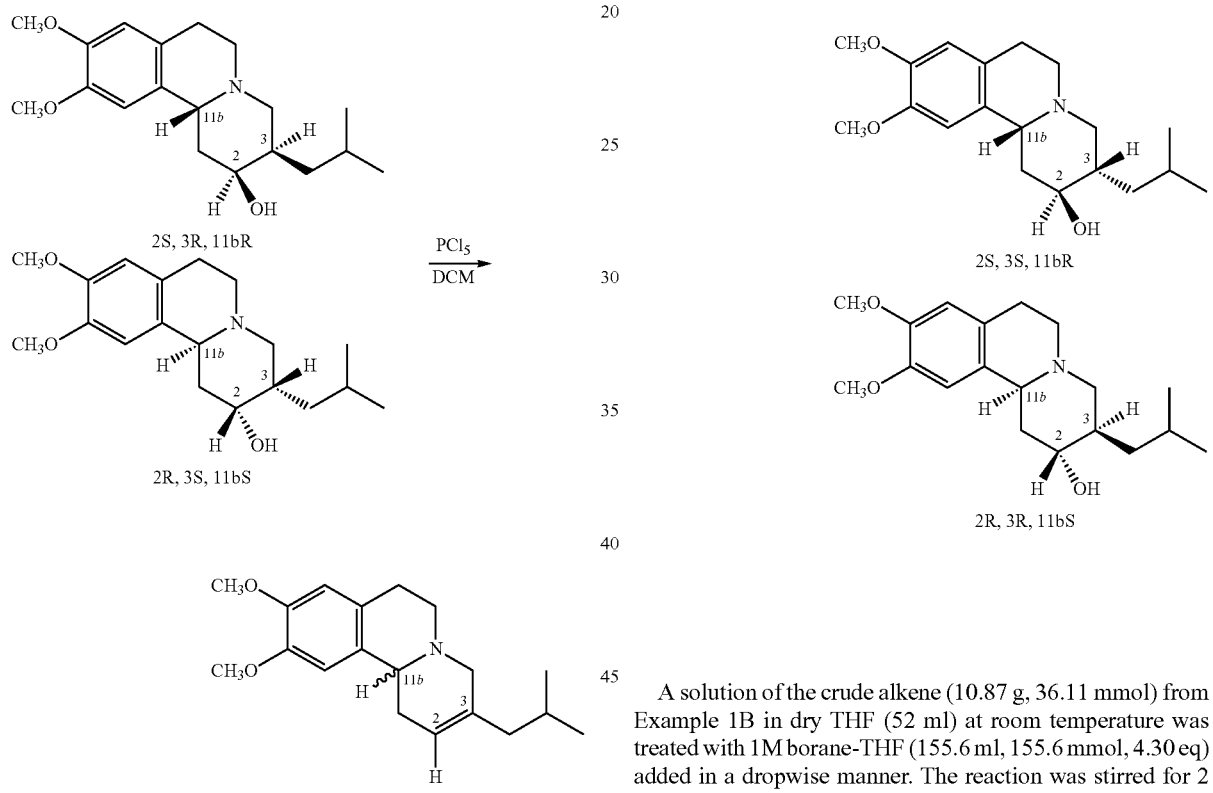

Phosphorous pentachloride (32.8 g, 157.5 mmol, 2.5 eq) was added in portions over 30 minutes to a stirred solution of the reduced tetrabenazine product from Example 1A (20 g, 62.7 mmol) in dichloromethane (200 ml) at 0° C. After the addition was complete, the reaction mixture was stirred at 0° C. for a further 30 minutes and the solution poured slowly into 2M aqueous sodium carbonate solution containing crushed ice (0° C.). Once the initial acid gas evolution had ceased the mixture was basified (ca. pH 12) using solid sodium carbonate.

The alkaline solution was extracted using ethyl acetate (800 ml) and the combined organic extracts dried over anhydrous magnesium sulphate. After filtration the solvent was removed at reduced pressure to afford a brown oil, which was A solution of the crude alkene (10.87 g, 36.11 mmol) from Example 1B in dry THF (52 ml) at room temperature was treated with 1M borane-THF (155.6 ml, 155.6 mmol, 4.30 eq) added in a dropwise manner. The reaction was stirred for 2 hours, water (20 ml) was added and the solution basified to pH 12 with 30% aqueous sodium hydroxide solution.

Aqueous 30% hydrogen peroxide solution (30 ml) was added to the stirred alkaline reaction mixture and the solution was heated to reflux for 1 hour before being allowed to cool. Water (100 ml) was added and the mixture extracted with ethyl acetate (3×250 ml). The organic extracts were combined and dried over anhydrous magnesium sulphate and after filtration the solvent was removed at reduced pressure to afford a yellow oil (9 g).

The oil was purified using preparative HPLC (Column: Lichrospher Si60, 5 μm, 250×21.20 mm, mobile phase: hexane:ethanol:dichloromethane (85:15:5); UV 254 nm, flow: 10 ml min$^{-1}$) at 350 mg per injection followed by concentration of the fractions of interest under vacuum. The product oil was then dissolved in ether and concentrated once more under vacuum to give the dihydrotetrabenazine racemate shown above as a yellow foam (5.76 g, 50%).

1D. Preparation of Mosher's Ester Derivatives

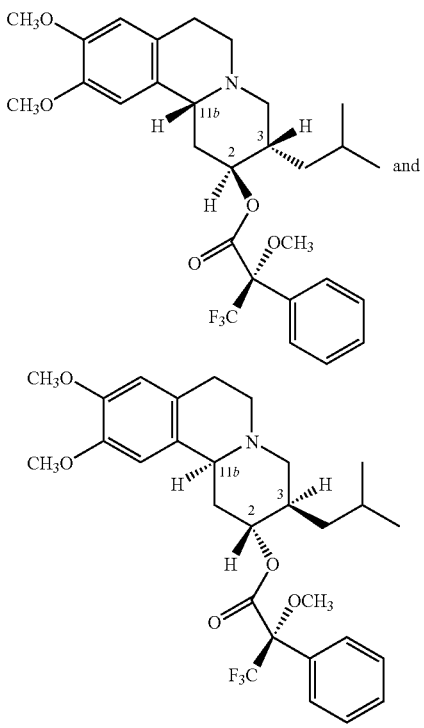

R-(+)-α-methoxy-α-trifluoromethylphenyl acetic acid (5 g, 21.35 mmol), oxalyl chloride (2.02 ml) and DMF (0.16 ml) were added to anhydrous dichloromethane (50 ml) and the solution was stirred at room temperature for 45 minutes. The solution was concentrated under reduced pressure and the residue was taken up in anhydrous dichloromethane (50 ml) once more. The resulting solution was cooled using an ice-water bath and dimethylaminopyridine (3.83 g, 31.34 mmol) was added followed by a pre-dried solution (over 4 Å sieves) in anhydrous dichloromethane of the solid product of Example 1C (5 g, 15.6 mmol). After stirring at room temperature for 45 minutes, water (234 ml) was added and the mixture extracted with ether (2×200 ml). The ether extract was dried over anhydrous magnesium sulphate, passed through a pad of silica and the product eluted using ether.

The collected ether eluate was concentrated under reduced pressure to afford an oil which was purified using column chromatography (silica, hexane:ether (10:1)). Evaporation of the collected column fractions of interest and removal of the solvent at reduced pressure gave a solid which was further purified using column chromatography (silica, hexane:ethyl acetate (1:1)) to give three main components which were partially resolved into Mosher's ester peaks 1 and 2.

Preparative HPLC of the three components (Column: 2×Lichrospher Si60, 5 μm, 250×21.20 mm, mobile phase: hexane:isopropanol (97:3), UV 254 nm; flow: 10 ml min$^{-1}$) at 300 mg loading followed by concentration of the fractions of interest under vacuum gave the pure Mosher's ester derivatives Peak 1 (3.89 g, 46.5%)
Peak 2 (2.78 g, 33%)

The fractions corresponding to the two peaks were subjected to hydrolysis to liberate the individual dihydrotetrabenazine isomers identified and characterised as Isomers A and B. Isomers A and B are each believed to have one of the following structures

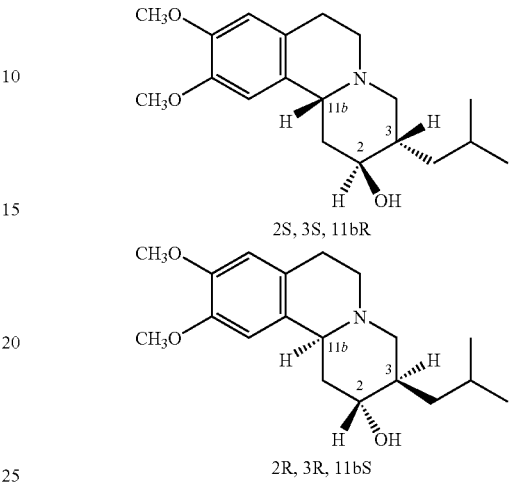

2S, 3S, 11bR 2R, 3R, 11bS

More specifically, Isomer B is believed to have the 2S, 3S, 11bR absolute configuration on the basis of the X-ray crystallography experiments described in Example 4 below.

1E. Hydrolysis of Peak 1 to Give Isomer A

Aqueous 20% sodium hydroxide solution (87.5 ml) was added to a solution of Mosher's ester peak 1 (3.89 g, 7.27 mmol) in methanol (260 ml) and the mixture stirred and heated to reflux for 150 minutes. After cooling to room temperature water (200 ml) was added and the solution extracted with ether (600 ml), dried over anhydrous magnesium sulphate and after filtration, concentrated under reduced pressure.

The residue was dissolved using ethyl acetate (200 ml), the solution washed with water (2×50 ml), the organic phase dried over anhydrous magnesium sulphate and after filtration, concentrated under reduced pressure to give a yellow foam. This material was purified by column chromatography (silica, gradient elution of ethyl acetate:hexane (1:1) to ethyl acetate). The fractions of interest were combined and the solvent removed at reduced pressure. The residue was taken up in ether and the solvent removed at reduced pressure once more to give Isomer A as an off-white foam (1.1 g, 47%).

Isomer A, which is believed to have the 2R,3R,11bS configuration (the absolute stereochemistry was not determined), was characterized by $^1$H-NMR, $^{13}$C-NMR, IR, mass spectrometry, chiral HPLC and ORD. The IR, NMR and MS data for isomer A are set out in Table 1 and the Chiral HPLC and ORD data are set out in Table 3.

1F. Hydrolysis of Peak 2 to Give Isomer B

Aqueous 20% sodium hydroxide solution (62.5 ml) was added to a solution of Mosher's ester peak 2 (2.78 g, 5.19 mmol) in methanol (185 ml) and the mixture stirred and heated to reflux for 150 minutes. After cooling to room temperature water (142 ml) was added and the solution extracted with ether (440 ml), dried over anhydrous magnesium sulphate and after filtration, concentrated under reduced pressure.

The residue was dissolved using ethyl acetate (200 ml), the solution washed with water (2×50 ml), the organic phase dried over anhydrous magnesium sulphate and after filtration, concentrated under reduced pressure. Petroleum ether (30-40° C.) was added to the residue and the solution concentrated under vacuum once more to give Isomer B as a white foam (1.34 g, 81%).

Isomer B, which is believed to have the 2S,3S,11bR configuration, was characterized by $^1$H-NMR, $^{13}$C-NMR, IR, mass spectrometry, chiral HPLC, ORD and X-ray crystallography. The IR, NMR and MS data for Isomer B are set out in Table 1 and the Chiral HPLC and ORD data are set out in Table 3. The X-ray crystallography data are set out in Example 4.

Example 2

Preparation of 2R,3S,11bR and 2S,3R,11bS Isomers of Dihydrotetrabenazine

2A. Preparation of 2,3-Dehydrotetrabenazine

A solution containing a racemic mixture (15 g, 47 mmol) of RR and SS tetrabenazine enantiomers in tetrahydrofuran was subjected to reduction with L-Selectride® by the method of Example 1A to give a mixture of the 2S,3R,11bR and 2R,3S,11bS enantiomers of dihydrotetrabenazine as a white powdery solid (12 g, 80%). The partially purified dihydrotetrabenazine was then dehydrated using PCl$_5$ according to the method of Example 1B to give a semi-pure mixture of 11bR and 11bS isomers of 2,3-dehydrotetrabenazine (the 11bR enantiomer of which is shown below) as a yellow solid (12.92 g, 68%).

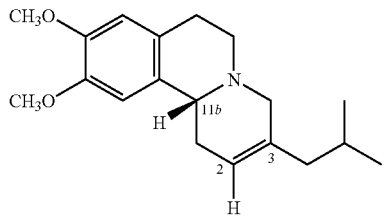

2B. Epoxidation of the Crude Alkene from Example 2A

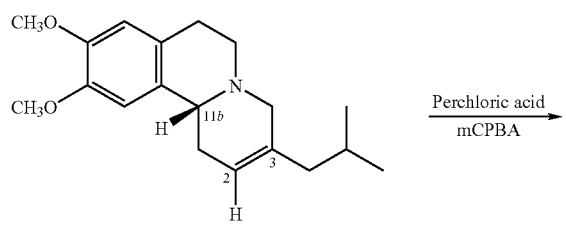

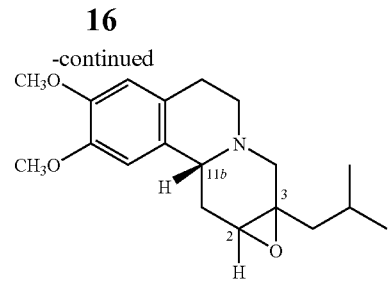

To a stirred solution of the crude alkene from Example 2A (12.92 g, 42.9 mmol) in methanol (215 ml) was added a solution of 70% perchloric acid (3.70 ml, 43 mmol) in methanol (215 ml). 77% 3-Chloroperoxybenzoic acid (15.50 g, 65 mmol) was added to the reaction and the resulting mixture was stirred for 18 hours at room temperature protected from light.

The reaction mixture was poured into saturated aqueous sodium sulphite solution (200 ml) and water (200 ml) added. Chloroform (300 ml) was added to the resulting emulsion and the mixture basified with saturated aqueous sodium bicarbonate (400 ml).

The organic layer was collected and the aqueous phase washed with additional chloroform (2×150 ml). The combined chloroform layers were dried over anhydrous magnesium sulphate and after filtration the solvent was removed at reduced pressure to give a brown oil (14.35 g, yield>100%–probable solvent remains in product). This material was used without further purification.

2C. Reductive Ring Opening of the Epoxide from 2B

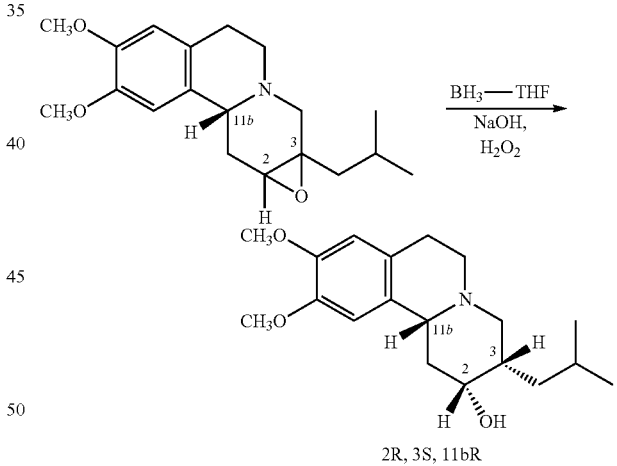

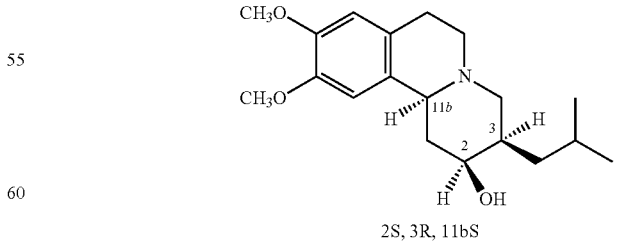

A stirred solution of the crude epoxide from Example 2B (14.35 g, 42.9 mmol, assuming 100% yield) in dry THF (80 ml) was treated slowly with 1M borane/THF (184.6 ml, 184.6 mmol) over 15 minutes. The reaction was stirred for two hours, water (65 ml) was added and the solution heated with stirring to reflux for 30 minutes.

After cooling, 30% sodium hydroxide solution (97 ml) was added to the reaction mixture followed by 30% hydrogen peroxide solution (48.6 ml) and the reaction was stirred and heated to reflux for an additional 1 hour.

The cooled reaction mixture was extracted with ethyl acetate (500 ml) dried over anhydrous magnesium sulphate and after filtration the solvent was removed at reduced pressure to give an oil. Hexane (230 ml) was added to the oil and the solution re-concentrated under reduced pressure.

The oily residue was purified by column chromatography (silica, ethyl acetate). The fractions of interest were combined and the solvent removed under reduced pressure. The residue was purified once more using column chromatography (silica, gradient, hexane to ether). The fractions of interest were combined and the solvents evaporated at reduced pressure to give a pale yellow solid (5.18 g, 38%).

2D. Preparation of Mosher's Ester Derivatives of the 2R,3S,11bR and 2S,3R,11bS Isomers of Dihydrotetrabenazine

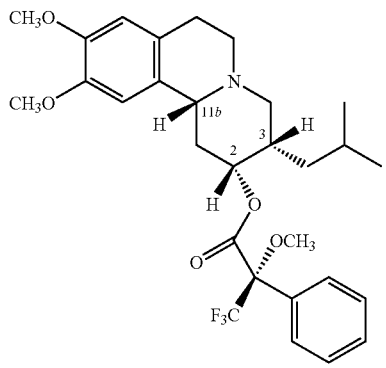

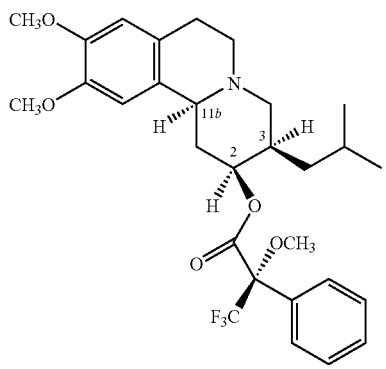

R-(+)-α-methoxy-α-trifluoromethylphenyl acetic acid (4.68 g, 19.98 mmol), oxalyl chloride (1.90 ml) and DMF (0.13 ml) were added to anhydrous dichloromethane (46 ml) and the solution stirred at room temperature for 45 minutes. The solution was concentrated under reduced pressure and the residue was taken up in anhydrous dichloromethane (40 ml) once more. The resulting solution was cooled using an ice-water bath and dimethylaminopyridine (3.65 g, 29.87 mmol) was added followed by a pre-dried solution (over 4 Å sieves) in anhydrous dichloromethane (20 ml) of the solid product of Example 2C (4.68 g, 14.6 mmol). After stirring at room temperature for 45 minutes, water (234 ml) was added and the mixture extracted with ether (2×200 ml). The ether extract was dried over anhydrous magnesium sulphate, passed through a pad of silica and the product eluted using ether.

The collected ether eluate was concentrated under reduced pressure to afford an oil which was purified using column chromatography (silica, hexane:ether (1:1)). Evaporation of the collected column fractions of interest and removal of the solvent at reduced pressure gave a pink solid (6.53 g)

Preparative HPLC of the solid (Column: 2× Lichrospher Si60, 5 μm, 250×21.20 mm; mobile phase hexane:isopropanol (97:3); UV 254 nm; flow: 10 ml min$^{-1}$) at 100 mg loading followed by concentration of the fractions of interest under vacuum gave a solid which was slurried with petroleum ether (30-40° C.) and collected by filtration to give the pure Mosher's ester derivatives
Peak 1 (2.37 g, 30%)
Peak 2 (2.42 g, 30%)

The fractions corresponding to the two peaks were subjected to hydrolysis to liberate the individual dihydrotetrabenazine isomers identified and characterised as Isomers C and D. Isomers C and D are each believed to have one of the following structures

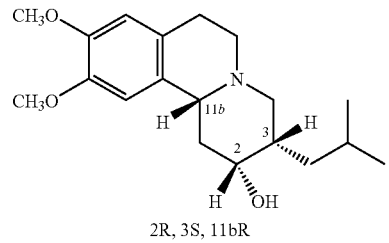

2R, 3S, 11bR

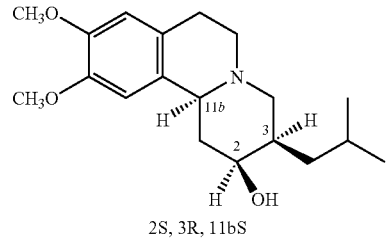

2S, 3R, 11bS

2F. Hydrolysis of Peak 1 to Give Isomer C

20% aqueous sodium hydroxide solution (53 ml) was added to a stirred solution of Mosher's ester peak 1 (2.37 g, 4.43 mmol) in methanol (158 ml) and the mixture stirred at reflux for 150 minutes. After cooling water (88 ml) was added to the reaction mixture and the resulting solution extracted with ether (576 ml). The organic extract was dried over anhydrous magnesium sulphate and after filtration the solvent removed at reduced pressure. Ethyl acetate (200 ml) was added to the residue and the solution washed with water (2×50 ml). The organic solution was dried over anhydrous magnesium sulphate and after filtration the solvent removed at reduced pressure.

This residue was treated with petroleum ether (30-40° C.) and the resulting suspended solid collected by filtration. The filtrate was concentrated at reduced pressure and the second batch of suspended solid was collected by filtration. Both collected solids were combined and dried under reduced pressure to give Isomer C (1.0 g, 70%).

Isomer C, which is believed to have either the 2R,3S,11bR or 2S,3R,11bS configuration (the absolute stereochemistry was not determined), was characterized by $^1$H-NMR, $^{13}$C-NMR, IR, mass spectrometry, chiral HPLC and ORD. The IR, NMR and MS data for Isomer C are set out in Table 2 and the Chiral HPLC and ORD data are set out in Table 4.

2G. Hydrolysis of Peak 2 to Give Isomer D

20% aqueous sodium hydroxide solution (53 ml) was added to a stirred solution of Mosher's ester peak 2 (2.42 g, 4.52 mmol) in methanol (158 ml) and the mixture stirred at reflux for 150 minutes. After cooling water (88 ml) was added to the reaction mixture and the resulting solution extracted with ether (576 ml). The organic extract was dried over anhydrous magnesium sulphate and after filtration the solvent removed at reduced pressure. Ethyl acetate (200 ml) was added to the residue and the solution washed with water (2×50 ml). The organic solution was dried over anhydrous magnesium sulphate and after filtration the solvent removed at reduced pressure.

This residue was treated with petroleum ether (30-40° C.) and the resulting suspended orange solid collected by filtration. The solid was dissolved in ethyl acetate:hexane (15:85) and purified by column chromatography (silica, gradient ethyl acetate:hexane (15:85) to ethyl acetate). The fractions of interest were combined and the solvent removed at reduced pressure. The residue was slurried with petroleum ether (30-40° C.) and the resulting suspension collected by filtration. The collected solid was dried under reduced pressure to give Isomer D as a white solid (0.93 g, 64%).

Isomer D, which is believed to have either the 2R,3S,11bR or 2S,3R,11bS configuration (the absolute stereochemistry was not determined), was characterized by $^1$H-NMR, $^{13}$C-NMR, IR, mass spectrometry, chiral HPLC and ORD. The IR, NMR and MS data for Isomer D are set out in Table 2 and the Chiral HPLC and ORD data are set out in Table 4.

In Tables 1 and 2, the infra red spectra were determined using the KBr disc method. The $^1$H NMR spectra were carried out on solutions in deuterated chloroform using a Varian Gemini NMR spectrometer (200 MHz.). The $^{13}$C NMR spectra were carried out on solutions in deuterated chloroform using a Varian Gemini NMR spectrometer (50 MHz). The mass spectra were obtained using a Micromass Platform II (ES$^+$ conditions) spectrometer. In Tables 3 and 4, the Optical Rotatory Dispersion figures were obtained using an Optical Activity PolAAr 2001 instrument in methanol solution at 24° C. The HPLC retention time measurements were carried out using an HP1050 HPLC chromatograph with UV detection.

Tables 1 and 2—Spectroscopic Data

TABLE 1

| Dihydrotetrabenazine isomer | $^1$H-NMR spectrum (CDCl$_3$) | $^{13}$C-NMR spectrum (CDCl$_3$) | IR Spectrum (KBr solid) | Mass Spectrum (ES$^+$) |
|---|---|---|---|---|
| Isomers A and B<br>2S, 3S, 11bR<br>OR<br>2R, 3R, 11bS | 6.67 δ 1H (s);<br>6.57 δ 1H (s);<br>3.84 δ 6H (s);<br>3.55 δ 1H (br. d);<br>3.08 δ 1H (m);<br>2.79 δ 2H (m);<br>2.55 δ 3H (m);<br>2.17 δ 1H (m);<br>1.72 δ 6H (m);<br>1.02 δ 1H (m);<br>0.88 δ 6H (t) | 147.7 δ;<br>147.6 δ;<br>130.5 δ;<br>127.6 δ;<br>112.1 δ;<br>108.4 δ;<br>70.5 δ;<br>57.5 δ;<br>56.5 δ;<br>56.3 δ;<br>54.8 δ;<br>53.2 δ;<br>40.4 δ;<br>40.1 δ;<br>36.0 δ;<br>28.8 δ;<br>26.2 δ;<br>23.7 δ;<br>22.9 δ | 2950 cm$^{-1}$;<br>2928 cm$^{-1}$;<br>2868 cm$^{-1}$;<br>2834 cm$^{-1}$;<br>1610 cm$^{-1}$;<br>1511 cm$^{-1}$;<br>1464 cm$^{-1}$;<br>1364 cm$^{-1}$;<br>1324 cm$^{-1}$;<br>1258 cm$^{-1}$;<br>1223 cm$^{-1}$;<br>1208 cm$^{-1}$;<br>1144 cm$^{-1}$;<br>1045 cm$^{-1}$;<br>1006 cm$^{-1}$;<br>870 cm$^{-1}$;<br>785 cm$^{-1}$;<br>764 cm$^{-1}$; | MH$^+$ 320 |

TABLE 2

| Dihydrotetrabenazine isomer | $^1$H-NMR spectrum (CDCl$_3$) | $^{13}$C-NMR spectrum (CDCl$_3$) | IR Spectrum (KBr solid) | Mass Spectrum (ES$^+$) |
|---|---|---|---|---|
| Isomers C and D<br><br>[Structure: 2R, 3S, 11bR]<br>OR<br>[Structure: 2S, 3R, 11bS] | 6.68 δ 1H (s);<br>6.58 δ 1H (s);<br>3.92 δ 1H (m);<br>3.84 δ 6H (s);<br>3.15 δ 1H (m);<br>2.87 δ 3H (m);<br>2.43 δ 4H (m);<br>1.81 δ 1H (m);<br>1.64 δ 4H (m);<br>1.21 δ 1H (m);<br>0.94 δ 3H (d);<br>0.89 δ 3H (d) | 147.8 δ;<br>147.7 δ;<br>130.4 δ;<br>127.2 δ;<br>112.0 δ;<br>108.3 δ;<br>72.4 δ;<br>61.2 δ;<br>58.3 δ;<br>56.5 δ;<br>56.3 δ;<br>52.7 δ;<br>38.6 δ;<br>36.7 δ;<br>34.4 δ;<br>29.6 δ;<br>26.5 δ;<br>24.4 δ;<br>22.5 δ | 3370 cm$^{-1}$;<br>2950 cm$^{-1}$;<br>2929 cm$^{-1}$;<br>1611 cm$^{-1}$;<br>1512 cm$^{-1}$;<br>1463 cm$^{-1}$;<br>1362 cm$^{-1}$;<br>1334 cm$^{-1}$;<br>1259 cm$^{-1}$;<br>1227 cm$^{-1}$;<br>1148 cm$^{-1}$;<br>1063 cm$^{-1}$;<br>1024 cm$^{-1}$;<br>855 cm$^{-1}$;<br>766 cm$^{-1}$ | MH$^+$ 320 |

Tables 3 and 4—Chromatography and ORD Data

TABLE 3

| Dihydrotetrabenazine isomer | Chiral HPLC Methods and Retention Times | | ORD (MeOH, 21° C.) |
|---|---|---|---|
| Isomers A and B<br><br>[Structure: 2S, 3S, 11bR]<br>OR<br>[Structure: 2R, 3R, 11bS] | Column:<br>Mobile phase:<br><br>Flow:<br>UV:<br>Retention times:<br>Isomer A<br>Isomer B | Chirex (S)-VAL, (R)-NEA, 250 × 4.6 mm<br>Hexane:1,2-dichloroethane:ethanol (36:62:2)<br>1.0 ml min$^{-1}$<br>254 nm<br><br>16.6 min<br>15.3 min | Isomer A<br>[α$_D$] −114.6°<br><br><br>Isomer B<br>[α$_D$] +23° |

TABLE 4

| Isomers C and D | | |
|---|---|---|
| (structure: 2R, 3S, 11bR) | Column: Chirex (S)-VAL, (R)-NEA, 250 × 4.6 mm<br>Mobile phase: Hexane:ethanol (92:8)<br>Flow: 1.0 ml min$^{-1}$<br>UV: 254 nm<br>Retention times:<br>Isomer C 20.3 min<br>Isomer D 19.4 min | Isomer C<br>[α$_D$] +150.9°<br>Isomer D<br>[α$_D$] −145.7° |
| OR | | |
| (structure: 2S, 3R, 11bS) | | |

Example 3

Alternative Method of Preparation of Isomer B and Preparation of Mesylate Salt

3A. Reduction of RR/SS Tetrabenazine

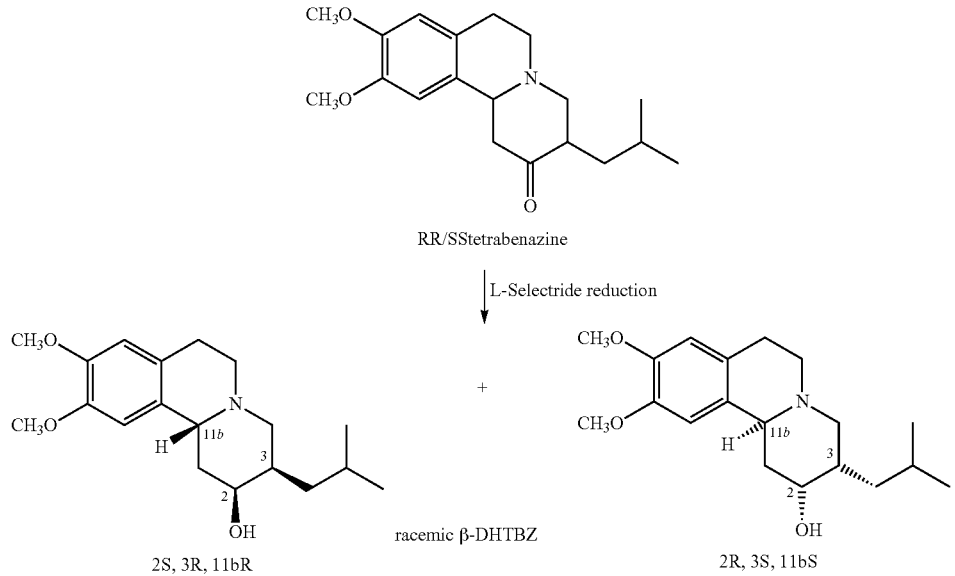

1M L-Selectride® in tetrahydrofuran (52 ml, 52 mmol, 1.1 eq) was added slowly over 30 minutes to a cooled (ice bath), stirred solution of tetrabenazine racemate (15 g, 47 mmol) in tetrahydrofuran (56 ml). After the addition was complete, the mixture was allowed to warm to room temperature and stirred for a further six hours. TLC analysis (silica, ethyl acetate) showed only very minor amounts of starting material remained.

The mixture was poured on to a stirred mixture of crushed ice (112 g), water (56 ml) and glacial acetic acid (12.2 g). The resulting yellow solution was washed with ether (2×50 ml) and basified by the slow addition of solid sodium carbonate (ca. 13 g). Pet-ether (30-40° C.) (56 ml) was added to the mixture with stirring and the crude β-DHTBZ was collected as a white solid by filtration.

The crude solid was dissolved in dichloromethane (ca. 150 ml) and the resulting solution washed with water (40 ml), dried using anhydrous magnesium sulphate, filtered and concentrated at reduced pressure to ca. 40 ml. A thick suspension of white solid was formed. Pet-ether (30-40° C.) (56 ml) was added and the suspension was stirred for fifteen minutes at laboratory temperature. The product was collected by filtration and washed on the filter until snow-white using pet-ether (30-40° C.) (40 to 60 ml) before air-drying at room temperature to yield β-DHTBZ (10.1 g, 67%) as a white solid. TLC analysis (silica, ethyl acetate) showed only one component.

3B. Preparation and Fractional Crystallisation of the Camphorsulphonic Acid Salt of Racemic β-DHTBZ The product of Example 3A and 1 equivalent of (S)-(+)-Camphor-10-sulphonic acid were dissolved with heating in the minimum amount of methanol. The resulting solution was allowed to cool and then diluted slowly with ether until formation of the resulting solid precipitation was complete. The resulting white crystalline solid was collected by filtration and washed with ether before drying.

The camphorsulphonic acid salt of (10 g) was dissolved in a mixture of hot absolute ethanol (170 ml) and methanol (30 ml). The resulting solution was stirred and allowed to cool. After two hours the precipitate formed was collected by filtration as a white crystalline solid (2.9 g). A sample of the crystalline material was shaken in a separating funnel with excess saturated aqueous sodium carbonate and dichloromethane. The organic phase was separated, dried over anhydrous magnesium sulphate, filtered and concentrated at reduced pressure. The residue was triturated using pet-ether (30-40° C.) and the organic solution concentrated once more. Chiral HPLC analysis of the salt using a Chirex (S)-VAL and (R)-NEA 250×4.6 mm column, and a hexane:ethanol (98:2) eluent at a flow rate of 1 ml/minute showed that the isolated β-DHTBZ was enriched in one enantiomer (e.e. ca. 80%).

The enriched camphorsulphonic acid salt (14 g) was dissolved in hot absolute ethanol (140 ml) and propan-2-ol (420 ml) was added. The resulting solution was stirred and a precipitate began to form within one minute. The mixture was allowed to cool to room temperature and stirred for one hour. The precipitate formed was collected by filtration, washed with ether and dried to give a white crystalline solid (12 g).

The crystalline material was shaken in a separating funnel with excess saturated aqueous sodium carbonate and dichloromethane. The organic phase was separated, dried over anhydrous magnesium sulphate, filtered and concentrated at reduced pressure. The residue was triturated using pet-ether (30-40° C.) and the organic solution concentrated once more to yield (after drying in vacuo.) (+)-β-DHTBZ (6.6 g, ORD+ 107.8°. The isolated enantiomer has e.e. >97%.

3C. Preparation of Isomer B

A solution of phosphorus pentachloride (4.5 g, 21.6 mmol, 1.05 eq) in dichloromethane (55 ml) was added steadily over ten minutes to a stirred, cooled (ice-water bath) solution of the product of Example 3B (6.6 g, 20.6 mmol) in dichloromethane (90 ml). When the addition was complete, the resulting yellow solution was stirred for a further ten minutes before pouring on to a rapidly stirred mixture of sodium carbonate (15 g) in water (90 ml) and crushed ice (90 g). The mixture was stirred for a further 10 minutes and transferred to a separating funnel.

Once the phases had separated, the brown dichloromethane layer was removed, dried over anhydrous magnesium sulphate, filtered and concentrated at reduced pressure to give the crude alkene intermediate as brown oil (ca. 6.7 g). TLC analysis (silica, ethyl acetate) showed that no (+)-β-DHTBZ remained in the crude product.

The crude alkene was taken up (dry nitrogen atmosphere) in anhydrous tetrahydrofuran (40 ml) and a solution of borane in THF (1 M solution, 2.5 eq, 52 ml) was added with stirring over fifteen minutes. The reaction mixture was then stirred at room temperature for two hours. TLC analysis (silica, ethyl acetate) showed that no alkene intermediate remained in the reaction mixture.

A solution of sodium hydroxide (3.7 g) in water (10 ml) was added to the stirring reaction mixture, followed by an aqueous solution of hydrogen peroxide (50%, ca. 7 ml) and the two-phase mixture formed was stirred at reflux for one hour. TLC analysis of the organic phase at this time (silica, ethyl acetate) showed the appearance of a product with Rf as expected for Isomer B. A characteristic non-polar component was also seen.

The reaction mixture was allowed to cool to room temperature and was poured into a separating funnel. The upper organic layer was removed and concentrated under reduced pressure to remove the majority of THF. The residue was taken up in ether (stabilised (BHT), 75 ml), washed with water (40 ml), dried over anhydrous magnesium sulphate, filtered and concentrated under reduced pressure to give a pale yellow oil (8.1 g).

The yellow oil was purified using column chromatography (silica, ethyl acetate:hexane (80:20), increasing to 100% ethyl acetate) and the desired column fractions collected, combined and concentrated at reduced pressure to give a pale oil which was treated with ether (stabilised, 18 ml) and concentrated at reduced pressure to give Isomer B as a pale yellow solid foam (2.2 g).

Chiral HPLC using the conditions set out in Example 3B confirmed that Isomer B had been produced in an enantiomeric excess (e.e.) of greater than 97%.

The optical rotation was measured using a Bellingham Stanley ADP220 polarimeter and gave an $[\alpha_D]$ of +123.5°.

3D. Preparation of the Mesylate Salt of Isomer B

The methanesulphonate salt of Isomer B was prepared by dissolving a mixture of 1 equivalent of Isomer B from Example 3C and 1 equivalent of methane sulphonic acid in the minimum amount of ethanol and then adding diethyl ether. The resulting white precipitate that formed was collected by filtration and dried in vacuo to give the mesylate salt in a yield of ca. 85% and a purity (by HPLC) of ca. 96%.

Example 4

X-Ray Crystallographic Studies on Isomer B

The (S)-(+)-Camphor-10-sulphonic acid salt of Isomer B was prepared and a single crystal was subjected to X-ray crystallographic studies under the following conditions:
Diffractometer: Nonius KappaCCD area detector (t/i scans and OJ scans to fill asymmetric unit).
Cell determination: DirAx (Duisenberg, A. J. M. (1992). *J. Appl. Cryst.* 25, 92-96.)
Data collection: Collect (Collect: Data collection software, R. Hooft, Nonius B. V, 1998)
Data reduction and cell refinement: Demo (Z. Otwinowski & W. Minor, *Methods in Enzymology* (1997) Vol. 276: *Macromolecular Crystallography*, part A, pp. 307-326; C. W. Carter, Jr & R. M. Sweet, Eds., Academic Press).

Absorption correction: Sheldrick, G. M. SADABS—Bruker Nonius area detector scaling and absorption correction—V2.\0
Structure solution: SHELXS97 (G. M. Sheldrick, *Acta Cryst.* (1990) A46 467-473).
Structure refinement: SHELXL97 (G. M. Sheldrick (1997), University of Göttingen, Germany)
Graphics: Cameron—A Molecular Graphics Package (D. M. Watkin, L. Pearce and C. K. Prout, Chemical Crystallography Laboratory, University of Oxford, 1993)
Special details: All hydrogen atoms were placed in idealised positions and refined using a riding model, except those of the NH and OH which were located in the difference map and refined using restraints. Chirality: Nl=R, Cl2=S, Cl3=S, Cl5=R, C21=S, C24=R The results of the studies are set out below in Tables A, B, C, D and E.

In the Tables, the label RUS0350 refers to Isomer B.

TABLE A

| | |
|---|---|
| Identification code | 2005bdy0585 (RUS0350) |
| Empirical formula | $C_{29}H_{45}NO_7S$ |
| Formula weight | 551.72 |
| Temperature | 120(2) K |
| Wavelength | 0.71073 Å |
| Crystal system | Orthorhombic |
| Space group | $P2_12_12_1$ |
| Unit cell dimensions | a = 7.1732(9) Å |
| | b = 12.941(2) Å |
| | c = 31.025(4) Å |
| Volume | 2880.1(7) Å$^3$ |
| Z | 4 |
| Density (calculated) | 1.272 Mg/m$^3$ |
| Absorption coefficient | 0.158 mm$^{-1}$ |
| F (000) | 1192 |
| Crystal | Colourless Slab |
| Crystal size | 0.2 × 0.2 × 0.04 mm$^3$ |
| θ range for data collection | 3.06 – 27.37° |
| Index ranges | $-8 \leq h \leq 9, -16 \leq k \leq 16, -36 \leq l \leq 39$ |
| Reflections collected | 36802 |
| Independent reflections | 6326 [$R_{int}$ = 0.0863] |
| Completeness to θ = 27.37° | 97.1% |
| Absorption correction | Semi-empirical from equivalents |
| Max. and min. transmission | 0.9937 and 0.9690 |
| Refinement method | Full-matrix least-squares on F$^2$ |
| Data/restraints/parameters | 6326/1/357 |
| Goodness-of-fit on F$^2$ | 1.042 |
| Final R indices [F$^2$ > 2σ(F$^2$)] | R1 = 0.0498, wR2 = 0.0967 |
| R indices (all data) | R1 = 0.0901, wR2 = 0.1108 |
| Absolute structure parameter | 0.04(8) |
| Extinction coefficient | 0.0059(7) |
| Largest diff. peak and hole | 0.236 and -0.336 e Å$^{-3}$ |

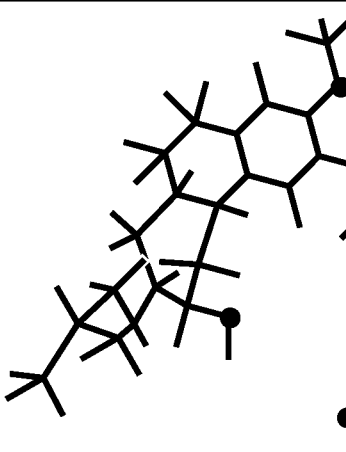

TABLE B

Atomic coordinates [×10$^4$], equivalent isotropic displacement parameters [Å$^2$ × 10$^3$] and site occupancy factors.

| Atom | x | y | z | Ueq | S.o.f. |
|---|---|---|---|---|---|
| N1 | 4839(3) | 11119(2) | 2180(1) | 24(1) | 1 |
| O1 | 2515(3) | 13171(1) | 349(1) | 31(1) | 1 |
| O2 | 5581(3) | 14030(1) | 598(1) | 32(1) | 1 |
| O3 | 9220(3) | 12834(2) | 2385(1) | 36(1) | 1 |
| C1 | 870(4) | 12674(2) | 190(1) | 36(1) | 1 |
| C2 | 3176(3) | 12838(2) | 739(1) | 25(1) | 1 |
| C3 | 2346(4) | 12109(2) | 997(1) | 25(1) | 1 |
| C4 | 3124(4) | 11821(2) | 1395(1) | 24(1) | 1 |
| C5 | 4773(3) | 12276(2) | 1527(1) | 23(1) | 1 |
| C6 | 5629(4) | 13024(2) | 1262(1) | 24(1) | 1 |
| C7 | 4861(4) | 13308(2) | 875(1) | 25(1) | 1 |
| C8 | 7189(4) | 14582(2) | 747(1) | 38(1) | 1 |
| C9 | 2182(3) | 11023(2) | 1673(1) | 28(1) | 1 |

TABLE B-continued

Atomic coordinates [×10$^4$], equivalent isotropic displacement parameters [Å$^2$ × 10$^3$] and site occupancy factors.

| Atom | x | y | z | Ueq | S.o.f. |
|---|---|---|---|---|---|
| C10 | 2759(3) | 11118(2) | 2137(1) | 26(1) | 1 |
| C11 | 5366(3) | 11096(2) | 2656(1) | 25(1) | 1 |
| C12 | 7292(4) | 11536(2) | 2747(1) | 25(1) | 1 |
| C13 | 7468(4) | 12663(2) | 2590(1) | 25(1) | 1 |
| C14 | 5988(4) | 12911(2) | 2252(1) | 25(1) | 1 |
| C15 | 5773(4) | 12010(2) | 1943(1) | 24(1) | 1 |
| C16 | 7734(4) | 11477(2) | 3232(1) | 28(1) | 1 |
| C17 | 7752(4) | 10418(2) | 3449(1) | 34(1) | 1 |
| C18 | 9198(6) | 9696(3) | 3249(1) | 65(1) | 1 |
| C19 | 8114(4) | 10562(2) | 3930(1) | 41(1) | 1 |
| C20 | 7509(4) | 8131(2) | 1250(1) | 31(1) | 1 |
| S1 | 7409(1) | 8792(1) | 1754(1) | 27(1) | 1 |
| O4 | 7758(2) | 7965(1) | 2064(1) | 30(1) | 1 |

TABLE B-continued

Atomic coordinates [×10$^4$], equivalent isotropic displacement parameters [Å$^2$ × 10$^3$] and site occupancy factors.

| Atom | x | y | z | Ueq | S.o.f. |
|---|---|---|---|---|---|
| O5 | 8831(3) | 9582(2) | 1760(1) | 49(1) | 1 |
| O6 | 5524(2) | 9221(1) | 1798(1) | 32(1) | 1 |
| O7 | 7406(3) | 6932(1) | 498(1) | 48(1) | 1 |
| C21 | 6858(3) | 8622(2) | 830(1) | 25(1) | 1 |
| C22 | 7154(4) | 7851(2) | 459(1) | 30(1) | 1 |
| C23 | 7073(4) | 8450(2) | 40(1) | 32(1) | 1 |
| C24 | 6648(3) | 9544(2) | 203(1) | 28(1) | 1 |
| C25 | 4742(3) | 8877(2) | 787(1) | 29(1) | 1 |
| C26 | 4742(3) | 8877(2) | 787(1) | 29(1) | 1 |
| C27 | 7773(4) | 9610(2) | 630(1) | 25(1) | 1 |

TABLE B-continued

Atomic coordinates [×10⁴], equivalent isotropic displacement parameters [Å² × 10³] and site occupancy factors.

| Atom | x | y | z | Ueq | S.o.f. |
|---|---|---|---|---|---|
| C28 | 7431(4) | 10628(2) | 868(1) | 29(1) | 1 |
| C29 | 9895(4) | 9489(2) | 569(1) | 36(1) | 1 |

$U_{eq}$ is defined as one third of the trace of the orthogonalized $U^{ij}$ tensor.

TABLE C

Bond lengths [Å] and angles [°].

| | | | |
|---|---|---|---|
| N1—C10 | 1.498(3) | C14—C15 | 1.518(3) |
| N1—C15 | 1.522(3) | C16—C17 | 1.526(3) |
| N1—C11 | 1.524(3) | C17—C18 | 1.527(4) |
| O1—C2 | 1.368(3) | C17—C19 | 1.527(3) |
| O1—C1 | 1.432(3) | C20—C21 | 1.525(3) |
| O2—C7 | 1.369(3) | C20—S1 | 1.784(2) |
| O2—C8 | 1.433(3) | S1—O5 | 1.4442(19) |
| O3—C13 | 1.425(3) | S1—O4 | 1.4607(17) |
| C2—C3 | 1.372(3) | S1—O6 | 1.4676(18) |
| C2—C7 | 1.417(3) | O7—C22 | 1.208(3) |
| C3—C4 | 1.407(3) | C21—C22 | 1.537(4) |
| C4—C5 | 1.384(3) | C21—C26 | 1.559(3) |
| C4—C9 | 1.506(3) | C21—C27 | 1.565(3) |
| C5—C6 | 1.411(3) | C22—C23 | 1.517(4) |
| C5—C15 | 1.516(3) | C23—C24 | 1.535(4) |
| C6—C7 | 1.372(3) | C24—C25 | 1.548(4) |
| C9—C10 | 1.504(3) | C24—C27 | 1.554(4) |
| C11—C12 | 1.521(3) | C25—C26 | 1.557(4) |
| C12—C16 | 1.540(3) | C27—C28 | 1.529(3) |
| C12—C13 | 1.544(3) | C27—C29 | 1.542(4) |
| C13—C14 | 1.524(3) | | |
| C10—N1—C15 | 113.33(19) | C12—C11—N1 | 113.43(19) |
| C10—N1—C11 | 109.46(18) | C11—C12—C16 | 110.5(2) |
| C15—N1—C11 | 111.96(19) | C11—C12—C13 | 111.7(2) |
| C2—O1—C1 | 116.6(2) | C16—C12—C13 | 109.84(19) |
| C7—O2—C8 | 116.27(19) | O3—C13—C14 | 106.0(2) |
| O1—C2—C3 | 125.5(2) | O3—C13—C12 | 111.1(2) |
| O1—C2—C7 | 115.0(2) | C14—C13—C12 | 111.0(2) |
| C3—C2—C7 | 119.5(2) | C15—C14—C13 | 110.1(2) |
| C2—C3—C4 | 121.5(2) | C5—C15—C14 | 114.3(2) |
| C5—C4—C3 | 119.2(2) | C5—C15—N1 | 112.0(2) |
| C5—C4—C9 | 120.3(2) | C14—C15—N1 | 108.7(2) |
| C3—C4—C9 | 120.5(2) | C17—C16—C12 | 118.4(2) |
| C4—C5—C6 | 119.4(2) | C16—C17—C18 | 112.2(2) |
| C4—C5—C15 | 124.1(2) | C16—C17—C19 | 108.7(2) |
| C6—C5—C15 | 116.6(2) | C18—C17—C19 | 110.8(3) |
| C7—C6—C5 | 121.3(2) | C21—C20—S1 | 122.51(18) |
| O2—C7—C6 | 125.4(2) | O5—S1—O4 | 112.93(11) |
| O2—C7—C2 | 115.4(2) | O5—S1—O6 | 112.47(12) |
| C6—C7—C2 | 119.2(2) | O4—S1—O6 | 111.93(11) |
| C10—C9—C4 | 111.7(2) | O5—S1—C20 | 108.81(13) |
| N1—C10—C9 | 111.0(2) | O4—S1—C20 | 102.60(11) |
| O6—S1—C20 | 107.44(12) | C23—C24—C25 | 106.4(2) |
| C20—C21—C22 | 109.0(2) | C23—C24—C27 | 103.3(2) |
| C20—C21—C26 | 117.3(2) | C25—C24—C27 | 102.3(2) |
| C22—C21—C26 | 102.1(2) | C24—C25—C26 | 102.9(2) |
| C20—C21—C27 | 123.4(2) | C25—C26—C21 | 104.2(2) |
| C22—C21—C27 | 100.21(19) | C28—C27—C29 | 107.8(2) |
| C26—C21—C27 | 101.7(2) | C28—C27—C24 | 112.0(2) |
| O7—C22—C23 | 126.4(2) | C29—C27—C24 | 113.7(2) |
| O7—C22—C21 | 125.9(2) | C28—C27—C21 | 116.5(2) |
| C23—C22—C21 | 107.7(2) | C29—C27—C21 | 112.3(2) |
| C22—C23—C24 | 101.3(2) | C24—C27—C21 | 94.27(19) |

TABLE D

Anisotropic displacement parameters [Å² × 10³].
The anisotropic displacement factor exponent takes the form:
$-2\pi^2[h^2 a^{*2} U^{11} + \ldots + 2 h k a^* b^* U^{12}]$.

| Atom | U¹¹ | U²² | U³³ | U²³ | U¹³ | U¹² |
|---|---|---|---|---|---|---|
| N1 | 26(1) | 24(1) | 23(1) | 2(1) | −1(1) | −3(1) |
| O1 | 37(1) | 30(1) | 24(1) | 3(1) | −7(1) | −4(1) |
| O2 | 41(1) | 31(1) | 25(1) | 5(1) | −2(1) | −10(1) |
| O3 | 26(1) | 49(1) | 32(1) | 7(1) | −3(1) | −9(1) |
| C1 | 41(2) | 36(2) | 32(2) | 3(1) | −9(1) | −8(2) |
| C2 | 30(2) | 24(2) | 22(1) | 1(1) | −1(1) | 2(1) |
| C3 | 25(1) | 26(1) | 24(1) | −3(1) | −2(1) | 2(1) |
| C4 | 26(2) | 22(1) | 23(1) | −1(1) | 2(1) | −1(1) |
| C5 | 24(1) | 22(1) | 23(1) | −2(1) | 1(1) | 0(1) |
| C6 | 26(1) | 22(1) | 24(1) | −3(1) | 2(1) | −5(1) |
| C7 | 30(2) | 22(1) | 22(1) | 2(1) | 4(1) | −4(1) |
| C8 | 45(2) | 34(2) | 36(2) | 5(1) | −2(1) | −20(2) |
| C9 | 23(1) | 32(1) | 29(2) | 3(1) | −1(1) | −4(1) |
| C10 | 26(1) | 29(1) | 25(1) | 2(1) | 0(1) | −5(1) |
| C11 | 31(1) | 25(1) | 20(1) | 2(1) | 0(1) | −2(1) |
| C12 | 26(1) | 26(1) | 23(1) | −1(1) | 1(1) | −1(1) |
| C13 | 26(1) | 28(1) | 23(1) | −1(1) | −1(1) | −2(1) |
| C14 | 30(2) | 22(2) | 24(1) | −1(1) | 1(1) | −1(1) |
| C15 | 22(1) | 22(1) | 28(1) | 2(1) | 0(1) | −4(1) |
| C16 | 31(1) | 28(1) | 24(1) | −1(1) | −3(1) | 3(1) |
| C17 | 46(2) | 31(2) | 25(1) | 1(1) | −7(1) | 0(2) |
| C18 | 106(3) | 46(2) | 41(2) | 6(2) | −1(2) | 31(2) |
| C19 | 51(2) | 41(2) | 31(2) | 9(2) | −7(1) | −4(2) |
| C20 | 30(2) | 34(2) | 29(1) | 2(1) | 3(1) | 9(2) |
| S1 | 27(1) | 30(1) | 24(1) | 4(1) | −2(1) | −5(1) |
| O4 | 31(1) | 36(1) | 23(1) | 9(1) | −1(1) | 0(1) |
| O5 | 53(1) | 58(1) | 37(1) | 13(1) | −11(1) | −35(1) |
| O6 | 34(1) | 35(1) | 28(1) | −3(1) | −2(1) | 10(1) |
| O7 | 81(2) | 25(1) | 40(1) | −1(1) | 12(1) | 6(1) |
| C21 | 26(1) | 25(1) | 24(1) | −1(1) | 3(1) | 2(1) |
| C22 | 35(2) | 25(2) | 31(2) | 0(1) | 1(1) | −1(1) |
| C23 | 40(2) | 30(2) | 25(1) | −2(1) | 1(1) | −2(1) |
| C24 | 28(1) | 29(2) | 26(2) | 2(1) | 2(1) | 2(1) |
| C25 | 30(2) | 34(2) | 29(2) | −1(1) | −2(1) | 0(1) |
| C26 | 26(1) | 34(2) | 28(2) | 0(1) | 1(1) | −5(1) |
| C27 | 23(1) | 26(1) | 26(1) | 0(1) | 2(1) | 0(1) |
| C28 | 31(1) | 26(1) | 30(1) | 0(1) | −2(1) | −6(1) |
| C29 | 29(2) | 41(2) | 40(2) | 0(2) | 2(1) | −3(1) |

TABLE E

Hydrogen coordinates [×10⁴] and isotropic displacement parameters [Å² × 10³].

| Atom | x | y | z | $U_{eq}$ | S.o.f |
|---|---|---|---|---|---|
| H98 | 5190(40) | 10528(15) | 2062(10) | 70(8) | 1 |
| H99 | 10030(50) | 12950(30) | 2575(12) | 70(8) | 1 |
| H1A | 1107 | 11933 | 156 | 54 | 1 |
| H1B | 529 | 12973 | −89 | 54 | 1 |
| H1C | −154 | 12777 | 395 | 54 | 1 |
| H3 | 1220 | 11793 | 904 | 30 | 1 |
| H6 | 6760 | 13337 | 1353 | 29 | 1 |
| H8A | 6872 | 14966 | 1009 | 58 | 1 |
| H8B | 7600 | 15065 | 523 | 58 | 1 |
| H8C | 8193 | 14091 | 810 | 58 | 1 |
| H9A | 814 | 11106 | 1651 | 33 | 1 |
| H9B | 2505 | 10324 | 1567 | 33 | 1 |
| H10A | 2250 | 11767 | 2259 | 32 | 1 |
| H10B | 2235 | 10534 | 2304 | 32 | 1 |
| H11A | 4431 | 11494 | 2822 | 30 | 1 |
| H11B | 5322 | 10372 | 2759 | 30 | 1 |
| H12 | 8230 | 11108 | 2589 | 30 | 1 |
| H13 | 7334 | 13145 | 2840 | 30 | 1 |
| H14A | 4783 | 13050 | 2397 | 30 | 1 |
| H14B | 6354 | 13538 | 2090 | 30 | 1 |
| H15 | 7056 | 11776 | 1864 | 29 | 1 |
| H16A | 8973 | 11796 | 3278 | 33 | 1 |
| H16B | 6813 | 11911 | 3386 | 33 | 1 |
| H17 | 6493 | 10098 | 3412 | 41 | 1 |
| H18A | 8906 | 9588 | 2944 | 97 | 1 |

TABLE E-continued

Hydrogen coordinates [×10⁴] and isotropic displacement parameters [Å² × 10³].

| Atom | x | y | z | $U_{eq}$ | S.o.f |
|---|---|---|---|---|---|
| H18B | 9176 | 9031 | 3400 | 97 | 1 |
| H18C | 10440 | 10005 | 3276 | 97 | 1 |
| H19A | 9329 | 10894 | 3971 | 62 | 1 |
| H19B | 8110 | 9887 | 4073 | 62 | 1 |
| H19C | 7135 | 10999 | 4054 | 62 | 1 |
| H20A | 8824 | 7924 | 1207 | 37 | 1 |
| H20B | 6787 | 7484 | 1286 | 37 | 1 |
| H23A | 6070 | 8190 | −151 | 38 | 1 |
| H23B | 8277 | 8423 | −116 | 38 | 1 |
| H24 | 6928 | 10107 | −8 | 33 | 1 |
| H25A | 3773 | 9195 | 153 | 37 | 1 |
| H25B | 4152 | 10235 | 426 | 37 | 1 |
| H26A | 3994 | 8237 | 764 | 35 | 1 |
| H26B | 4300 | 9279 | 1039 | 35 | 1 |
| H28A | 8160 | 10638 | 1135 | 44 | 1 |
| H28B | 6103 | 10692 | 936 | 44 | 1 |
| H28C | 7811 | 11207 | 684 | 44 | 1 |
| H29A | 10358 | 10042 | 381 | 54 | 1 |
| H29B | 10159 | 8817 | 436 | 54 | 1 |
| H29C | 10517 | 9531 | 849 | 54 | 1 |

TABLE 6

Hydrogen bonds [Å and °].

| D—H...A | d(D—H) | d(H...A) | d(D...A) | ∠(DHA) |
|---|---|---|---|---|
| N1—H98...O6 | 0.885(10) | 1.895(12) | 2.773(3) | 171(3) |
| N1—H98...S1 | 0.885(10) | 2.914(14) | 3.771(2) | 163(3) |
| O3—H99...O4$^i$ | 0.84(4) | 1.94(4) | 2.766(3) | 165(3) |
| O3—H99...S1$^i$ | 0.84(4) | 2.98(4) | 3.811(2) | 169(3) |

Symmetry transformations used to generate equivalent atoms:
$^i$ −x + 2, y + 1/2, −z + 1/2

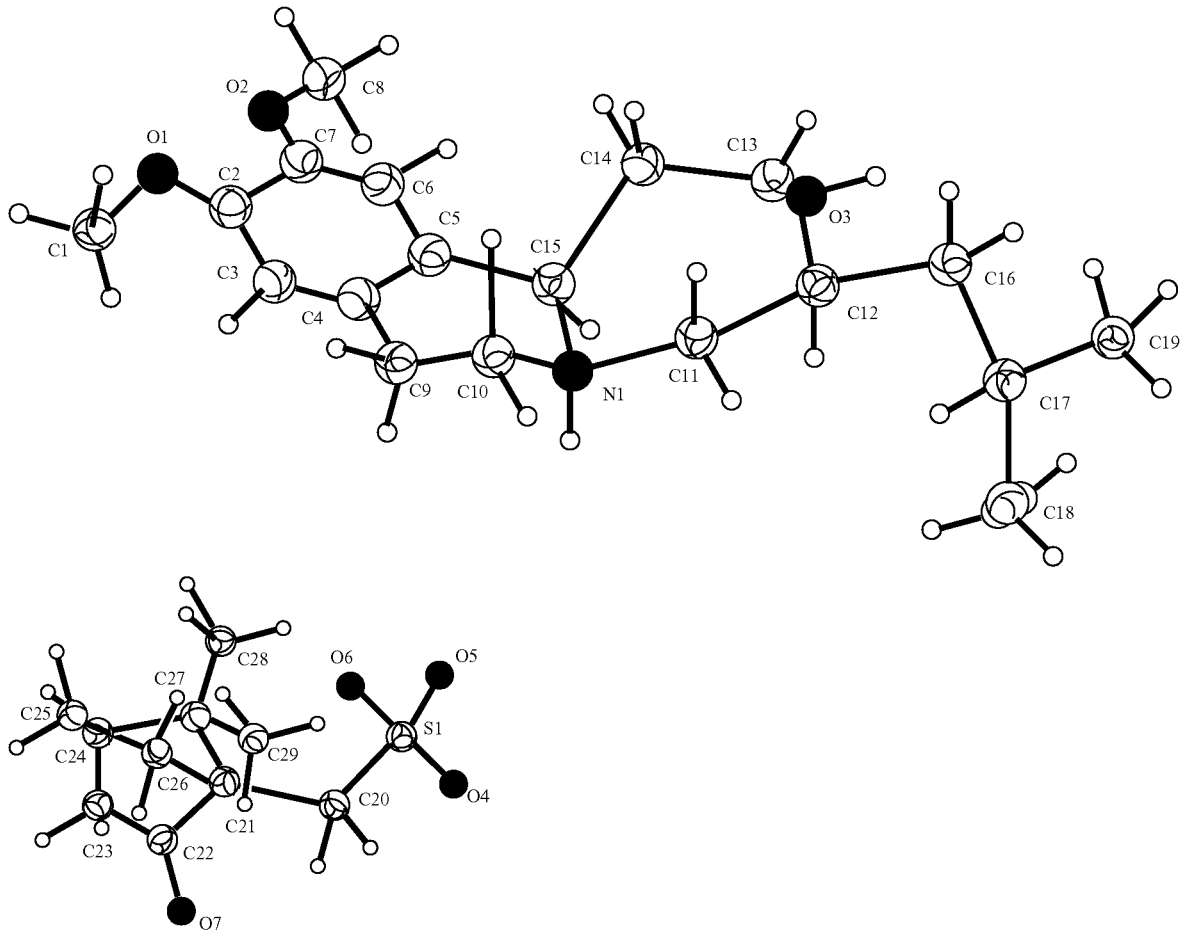

Thermal ellipsoids drawn at the 30% probability level

On the basis of the data set out above, Isomer B is believed to have the 2S,3S,11bR configuration, which corresponds to Formula (Ia):

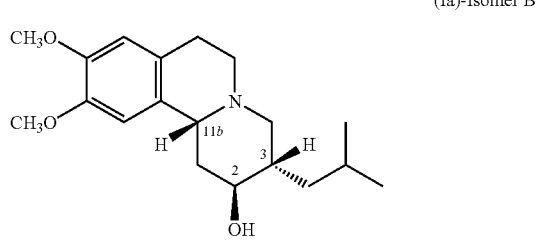

(Ia)-Isomer B

Isomer A, by elimination, must therefore have the 2R,3R, 11bS configuration, which corresponds to Formula (Ib):

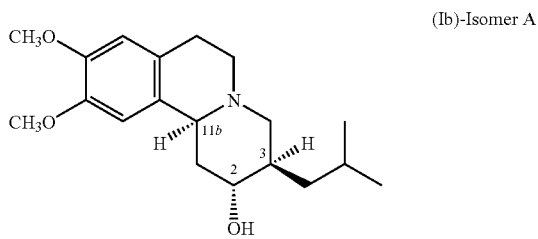

(Ib)-Isomer A

Example 5

Cognitive Function: An Investigation into the Efficacy of Isomer A to Improve a Cognitive Deficit Induced by Sub-chronic PCP in the Novel Object Recognition Task One of the symptoms of dementia is the progressive development of a cognitive deficit. Certain pre-clinical tests allow the observation of relatively subtle cognitive deficits in the rat. The cognitive deficits observed are seen in behaviours such as working memory deficits which may be measured by recognition tasks such as the novel object recognition (NOR) paradigm. A recognition memory task allows the comparison between presented stimuli and previously stored information. Ennaceur & Delacour, *Behav. Brain Res.* 31: 47-59 (1988) described the NOR test in rats which was based on the differential exploration of familiar and new objects. The NOR test is a non-rewarded, ethologically relevant paradigm based on the spontaneous exploratory behaviour of rats which measures working memory. Each session consists of two trials. In the first trial, the rats are exposed to two identical objects in an open field. During the second trial, rats are exposed to two dissimilar objects, one familiar object from the first trial and one new object. Object recognition in rats can be measured as the difference in time spent exploring the familiar and the new object. Rats have been shown to spend more time exploring the new object. It was found that rats are able to discriminate between the familiar and the novel object when the inter-trial interval is between 1 minute and 1-5 hours, but not when it is greater than 24 hours, although this effect may be sex dependent in the rat (Sutcliffe et al, *A preliminary investigation into the effects of gender on cognition in male and female rats using the novel object recognition paradigm*. Presented at the 96th meeting of the Society for Endocrinology, 7-9 Nov. 2005). The duration of each trial is also important as a preference for the novel object only lasts during the first 1 or 2 minutes, after which time preference diminishes as both objects become familiar and are explored equally.

Grayson and Neill (*J. Psychopharmacology* 18: A55, 2004; and Proceedings of the BPS at http://wwwpA2online.org/vol12issue4-abst077P.html. 2005) have demonstrated a selective deficit in this task induced by acute and sub-chronic treatment with PCP. The deficit is only observed in the retention phase of the task, suggesting a specific and relatively subtle cognitive impairment. Thus behaviour in the acquisition phase of the test (and locomotor activity) is unaffected by PCP treatment. The effects of PCP in this paradigm may represent a selective deficit in working memory.

Object of the Experiment

The abovementioned rodent model was used to assess the effects of the Isomer A on sub-chronic PCP-induced deficits in working memory using the novel object recognition (NOR) paradigm. The working hypothesis was that both acute and sub-chronic treatment with Isomer A will attenuate the selective working memory deficit induced by sub-chronic PCP as measured in the NOR test paradigm. Female rats were used in this paradigm as it has previously been found that males to be less sensitive to the deficit induced by PCP (Grayson and Neill, idem.) and females show more robust performance following increasing inter-trial intervals compared with male rats (Sutcliffe et al, idem).

Methods

The Novel Object Recognition Paradigm:

Habituation.

Rats are allowed to habituate to the empty test box and the behavioural test room environment for 1 hour on day 1. Prior to behavioural testing on day 2 rats are given a further 3 minutes habituation.

Behavioural Testing.

Following the 3 minute habituation period, the rats are given two 3 minute trials (T1 and T2) which are separated by a 1 minute inter-trial interval in the home cage during which the objects are changed.

T1=Trial 1, the Acquisition Trial.

In this trial, the animals are allowed to explore two identical objects (A1 and A2) for 3 minutes.

T2=Trial 2, the Retention Trial.

In this trial, the animals explore a familiar object (A) from T1 and a novel object (B) for 3 minutes. The familiar object presented during T2 is a duplicate of the object presented in T1 in order to avoid any olfactory trails.

Object Exploration.

The object exploration is defined by animals licking, sniffing or touching the object with the forepaws whilst sniffing, but not leaning against, turning around, standing or sitting on the object. The exploration time (s) of each object (A1, A2, A and B) in each trial are recorded using two stopwatches and the following factors are calculated:

Total exploration time of both objects in the acquisition trial(s).

Total exploration time of both objects in the retention trial (s).

Habituation of exploratory activity. The LMA includes the exploration time, as measured by the number of lines crossed, for both the trials.

Discrimination index, which is calculated as shown below;

(time spent exploring novel object−time spent exploring familiar object)÷total time spent in exploring the objects Behaviour in all trials was recorded on video for subsequent blind scoring.

Subjects 50 female hooded-Lister rats (Harlan, UK) were used as subjects for these studies. Rats were housed in groups of 5 under standard laboratory conditions under a 12 hr light:dark cycle, lights on at 0700 hr. All testing was carried out in the light phase. Food and water were freely provided. All experiments were conducted in accordance with the Animals Scientific Procedures Act, U.K. 1986 and were approved by the University of Bradford ethical review panel.

Drugs

Rats were randomly assigned to two treatment groups and treated with vehicle, n=10 (distilled water, ip) or PCP, n=40 (2 mg/kg, ip) twice daily for 7 days. Phencyclidine hydrochloride (PCP, Sigma, UK) was dissolved in distilled water. This was followed by a 7 day wash out period before the rats were tested. Isomer A was dissolved in distilled water and administered via the oral route at doses of 3, 10 and 30 mg/kg, 30 minutes prior to testing. Risperidone (0.2 mg/kg) was prepared in distilled water and injected i.p. 30 minutes prior to testing. All drugs were administered in a volume of 1 ml/kg. All drug doses were calculated as base equivalent weight.

Statistical Analysis

All data are expressed as mean±s.e.m (n=7-10 per group) and were analysed by a two way ANOVA (factors are; drug and exploration time of the two objects) with further analysis by a post-hoc student's t-test (time spent exploring objects) or Dunnett's t-test (LMA and DI).

Drug Treatment

Groups of rats (n=7-10) were tested in the NOR paradigm as described above. Rats were tested for their performance in the task following sub-chronic treatment with PCP (2 mg/kg i.p. twice daily for 7 days followed by 7 days drug-free period) or vehicle followed by acute treatment with Isomer A, risperidone or vehicle. Rats were randomly assigned to the drug treatment groups and received vehicle or Isomer A (3.0, 10 and 30 mg/kg) p.o. 30 minutes prior to behavioural testing.

Results

The results are shown in FIGS. 1 to 4.

FIG. 1 illustrates the mean exploration time of identical objects in the acquisition phase-T1—following acute administration of Isomer A (3.0-30 mg/kg, p.o) and risperidone (Risp 0.2 mg/kg, i.p) in sub-chronic PCP (2 mg/kg, i.p twice daily for seven days) and vehicle treated rats.

FIG. 2 illustrates the ability of acute Isomer A (3-30 mg/kg, p.o) and risperidone (Risp 0.2 mg/kg, i.p) to attenuate the effect of sub-chronic PCP on the exploration time (s) of a familiar object and a novel object in a 3 minute retention trial in female hL rats. Significant difference between time spent exploring the familiar and novel object *$P<0.05$– ***$P<0.001$.

Figure 3:
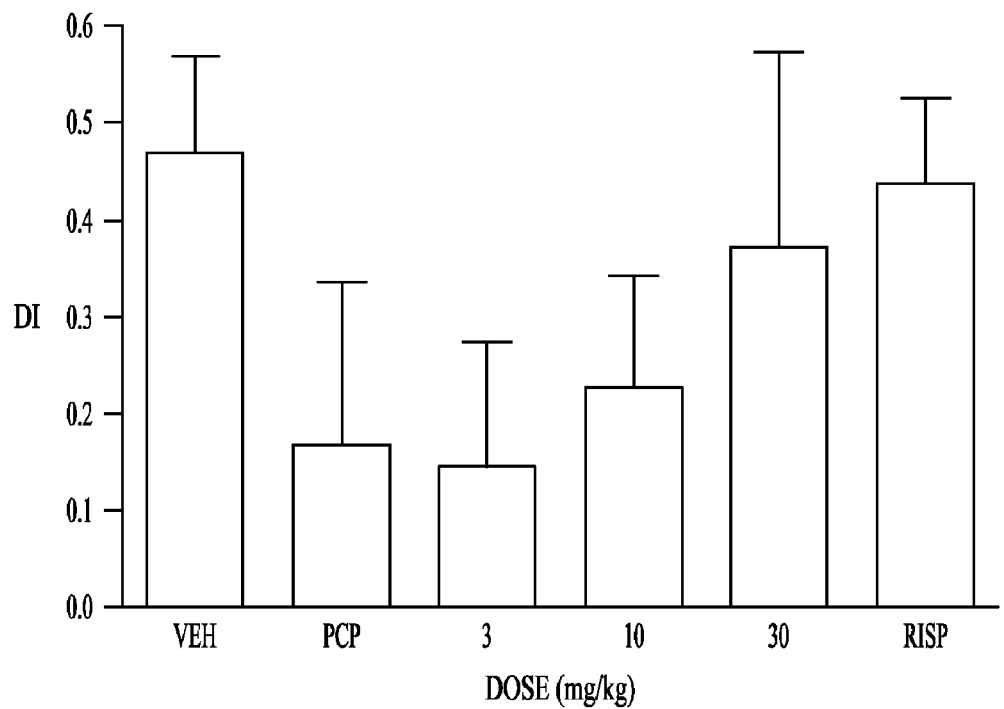
FIG. 3 illustrates the effect of Isomer A (3-30 mg/kg, p.o.) and risperidone (Risp 0.2 mg/kg, i.p.) on the effect of sub-chronic PCP (2 mg/kg, i.p twice daily for seven days) treatment on the discrimination index (DI).

FIG. 3 illustrates the effect of Isomer A (3-30 mg/kg, p.o.) and risperidone (Risp 0.2 mg/kg, i.p.) on the effect of sub-chronic PCP (2 mg/kg, i.p twice daily for seven days) treatment on the discrimination index (DI).

Figure 4:
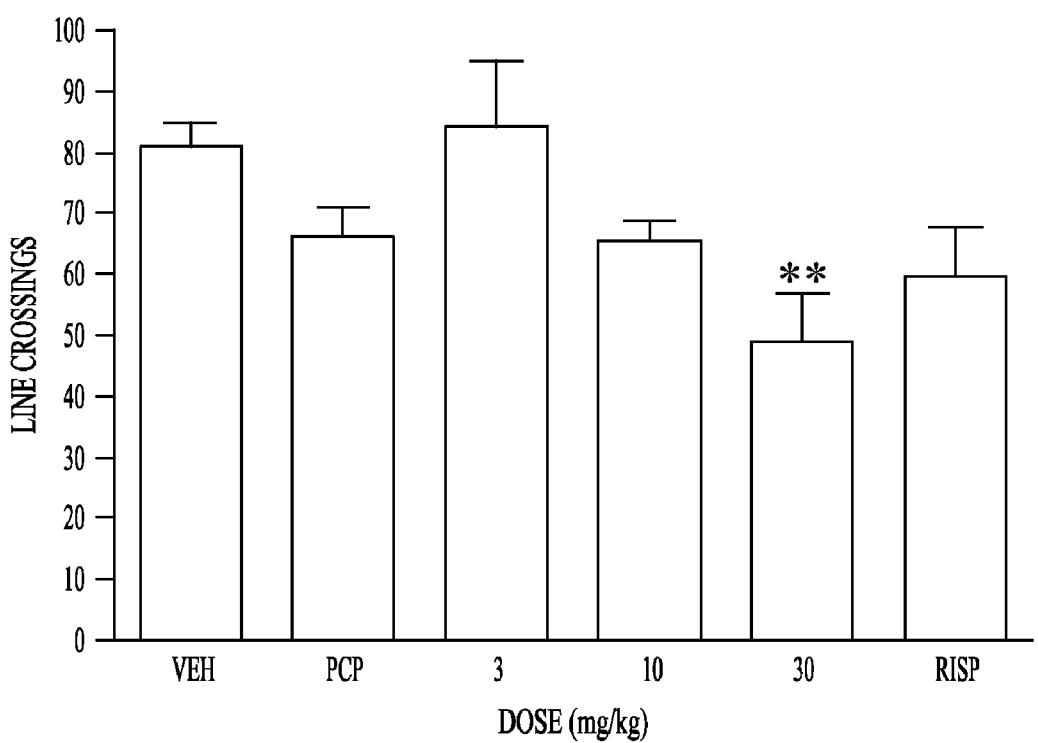
FIG. 4 illustrates the effect of acute administration (3-30 mg/kg, p.o.) of Isomer A and risperidone (Risp 0.2 mg/kg, i.p) in sub-chronically PCP treated rats on the total number of line crossings in the novel object recognition task (T1+T2). **p<0.01; significant reduction in number of line crossings compared with the vehicle control group.

FIG. 4 illustrates the effect of acute administration (3-30 mg/kg, p.o.) of Isomer A and risperidone (Risp 0.2 mg/kg, i.p) in sub-chronically PCP treated rats on the total number of line crossings in the novel object recognition task (T1+T2). **$p<0.01$; significant reduction in number of line crossings compared with the vehicle control group.

Acute PCP (0.5-2.0 mg/kg ip) and sub-chronic PCP (2 mg/kg i.p. twice daily for 7 days followed by 7 days drug-free period) produce a selective cognitive deficit in the retention phase of the NOR task in female rats (Grayson and Neill, 2004; 2005a). The atypical antipsychotic agent clozapine (1-5 mg/kg), but not haloperidol (0.05-0.075 mg/kg) significantly improved (and prevented, Idris et al, 2005) the deficit induced by sub-chronic PCP in this paradigm (Grayson and Neill, 2005a). The present results add to this existing data and show that Isomer A also has efficacy to attenuate the sub-chronic PCP-induced deficit in a manner similar to the atypical antipsychotic, risperidone.

The effects of acute treatment with Isomer A were selective for the retention phase of the NOR task (FIG. 2). Its effects are consistent with improvement of working memory deficits induced by PCP in a paradigm with some validity for the pathology of schizophrenia. This effect was significant at the highest dose of Isomer (30 mg/kg).

In contrast, Isomer A had no effect on exploration of two identical objects in the acquisition phase of the task, FIG. 1. 30 mg/kg of Isomer A also had a significant effect to reduce locomotor activity in the test arena, FIG. 4. This was shown as a reduction in the number of lines crossed in the novel object arena in T1 and T2. Observation of the behaviour of the rats suggested that they spent more time in object than environment exploration which reduced their overall activity score in the box. They did not appear sedated. Data shown in FIG. 3 show that sub-chronic PCP treatment induced a reduction in the discrimination index, and that this was improved following 30 mg/kg of Isomer A and 0.2 mg/kg of risperidone: however, none of these effects reached statistical significance.

The results set out herein suggest that Isomer A may have some therapeutic value in improvement of cognitive deficit symptoms.

Example 6

Pharmaceutical Compositions (i) Tablet Formulation—I

A tablet composition containing the dihydrotetrabenazine of the invention is prepared by mixing 50 mg of the dihydrotetrabenazine with 197 mg of lactose (BP) as diluent, and 3 mg magnesium stearate as a lubricant and compressing to form a tablet in known manner.

(ii) Tablet Formulation—II

A tablet composition containing the dihydrotetrabenazine of the invention is prepared by mixing the compound (25 mg) with iron oxide, lactose, magnesium stearate, starch maize white and talc, and compressing to form a tablet in known manner.

(iii) Capsule Formulation

A capsule formulation is prepared by mixing 100 mg of the dihydrotetrabenazine of the invention with 100 mg lactose and filling the resulting mixture into standard opaque hard gelatin capsules.

EQUIVALENTS

It will readily be apparent that numerous modifications and alterations may be made to the specific embodiments of the invention described above without departing from the principles underlying the invention. All such modifications and alterations are intended to be embraced by this application.

The invention claimed is:

1. A method of treating dementia or a cognitive deficit associated with dementia in a patient suffering from Alzheimer's disease, which method comprises administering to the patient a therapeutically effective amount of a 3,11b-cis-dihydrotetrabenazine or a pharmaceutically acceptable salt thereof, to thereby treat dementia or a cognitive deficit associated with dementia in the patient.

2. The method of claim 1, wherein the 3,11b-cis-dihydrotetrabenazine, or a pharmaceutically acceptable salt thereof, is a 2S,3S,11bR isomer of 3,11b-cis-dihydrotetrabenazine having the formula (Ia):

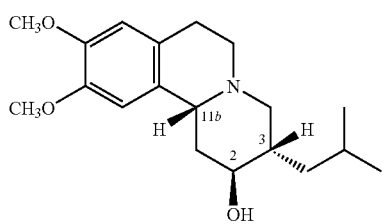

(Ia)

or a pharmaceutically acceptable salt thereof.

3. The method of claim 1, wherein the 3,11b-cis-dihydrotetrabenazine, or a pharmaceutically acceptable salt thereof, is a 2S,3R,11bS isomer of 3,11b-cis-dihydrotetrabenazine having the formula (Ib):

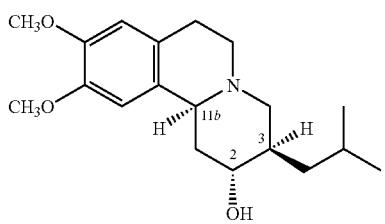

(Ib)

or a pharmaceutically acceptable salt thereof.

4. The method of claim 1, wherein the 3,11b-cis-dihydrotetrabenazine, or a pharmaceutically acceptable salt thereof, is a 2S,3S,11bR isomer of 3,11b-cis-dihydrotetrabenazine having the formula (Ic):

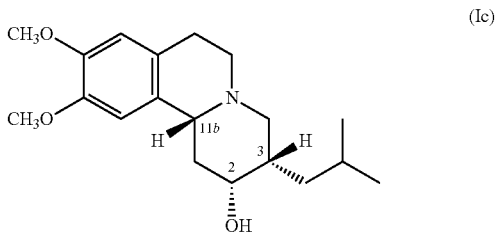

(Ic)

or a pharmaceutically acceptable salt thereof.

5. The method of claim 1, wherein the 3,11b-cis-dihydrotetrabenazine, or a pharmaceutically acceptable salt thereof, is a 2S,3S,11bS isomer of 3,11b-cis-dihydrotetrabenazine having the formula (Id):

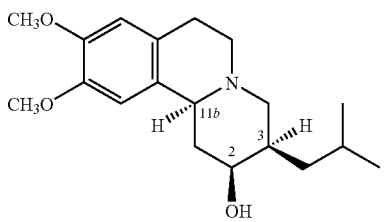

or a pharmaceutically acceptable salt thereof.

6. The method of claim 1, wherein the 3,11b-cis-dihydrotetrabenazine is a free base.

7. The method of claim 1, wherein the pharmaceutically acceptable salt of 3,11b-cis-dihydrotetrabenazine is an acid addition salt.

8. The method of claim 1, wherein the salt is a methane sulphonate salt.

9. The method of claim 1, wherein the dementia arises from or is associated with accumulation of amyloid plaques in the brain.

10. The method of claim 1, wherein the dementia is a form of dementia arising from an amyloidopathy.

* * * * *

UNITED STATES PATENT AND TRADEMARK OFFICE
CERTIFICATE OF CORRECTION

| | | |
|---|---|---|
| PATENT NO. | : 7,956,065 B2 | Page 1 of 1 |
| APPLICATION NO. | : 12/555695 | |
| DATED | : June 7, 2011 | |
| INVENTOR(S) | : Philip P. Nichols | |

It is certified that error appears in the above-identified patent and that said Letters Patent is hereby corrected as shown below:

In column 37, line 28, in claim 3, delete "2S," and insert -- 2R, --, therefor.

In column 38, line 1, in claim 4, delete "2S," and insert -- 2R, --, therefor.

In column 38, line 18, in claim 5, delete "3S," and insert -- 3R, --, therefor.

Signed and Sealed this
Ninth Day of August, 2011

David J. Kappos
*Director of the United States Patent and Trademark Office*